United States Patent
Tran et al.

(10) Patent No.: US 11,911,610 B2
(45) Date of Patent: Feb. 27, 2024

(54) METHODS FOR RESTORING SENSITIVITY TO TTFIELDS IN TTFIELDS-RESISTANT CANCER CELLS WITH PTGER3 INHIBITORS

(71) Applicant: Novocure GmbH, Root (CH)

(72) Inventors: David Tran, Gainesville, FL (US); Son Bang Le, Gainesville, FL (US); Dongjiang Chen, Gainesville, FL (US)

(73) Assignee: Novocure GmbH, Root (CH)

( * ) Notice: Subject to any disclaimer, the term of this patent is extended or adjusted under 35 U.S.C. 154(b) by 546 days.

(21) Appl. No.: 16/832,572

(22) Filed: Mar. 27, 2020

(65) Prior Publication Data

US 2020/0306531 A1 Oct. 1, 2020

Related U.S. Application Data

(60) Provisional application No. 62/849,535, filed on May 17, 2019, provisional application No. 62/826,078, filed on Mar. 29, 2019.

(51) Int. Cl.
| | |
|---|---|
| *A61K 31/192* | (2006.01) |
| *A61K 31/415* | (2006.01) |
| *A61N 1/20* | (2006.01) |
| *A61P 35/00* | (2006.01) |

(52) U.S. Cl.
CPC .......... *A61N 1/205* (2013.01); *A61K 31/192* (2013.01); *A61K 31/415* (2013.01); *A61P 35/00* (2018.01)

(58) Field of Classification Search
CPC ........ A61N 1/205; A61K 31/192; A61P 35/00
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |

(Continued)

FOREIGN PATENT DOCUMENTS

| | | |
|---|---|---|
| WO | 2010118010 A1 | 10/2010 |
| WO | 2019029351 A1 | 2/2019 |

OTHER PUBLICATIONS

Webpage printout of Pubmed.com, search of "PTGER3 and cancer", pp. 1-2, accessed Sep. 6, 2022. (Year: 2022).*

(Continued)

*Primary Examiner* — Craig D Ricci
*Assistant Examiner* — Janet L Coppins
(74) *Attorney, Agent, or Firm* — Potomac Law Group, PLLC

(57) ABSTRACT

Methods of reducing the viability of cancer cells, preventing cancer cells of a subject from developing resistance to TTFields, and restoring sensitivity of cancer cells to TTFields by recommending or prescribing a PTGER3 inhibitor to a subject and applying an alternating electric field to the cancer cells are provided. In some instances, sensitivity of cancer cells to TTFields can be restored with one or more PTGER3 inhibitors (e.g., NSAIDs, cox2 inhibitors).

6 Claims, 23 Drawing Sheets

(56) References Cited

U.S. PATENT DOCUMENTS

| | | |
|---|---|---|
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2006/0167499 A1 | 7/2006 | Palti |
| 2007/0225766 A1 | 9/2007 | Palti |
| 2007/0239213 A1 | 10/2007 | Palti |
| 2009/0076366 A1 | 3/2009 | Palti |
| 2010/0074896 A1 | 3/2010 | Dore et al. |
| 2012/0029419 A1 | 2/2012 | Paiti |
| 2012/0283726 A1 | 11/2012 | Palti |
| 2013/0244932 A1 | 9/2013 | Keller et al. |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |

OTHER PUBLICATIONS

Webpage printout of Pubmed.com, search "aspirin and cancer", pp. 1-6, accessed Sep. 6, 2022. (Year: 2022).*

Pozzoli et al. J Cell Physiol. 2019;234:15459-15471. (Year: 2019).*

Rehman et al. Neurosurg Focus 38 (3):E14, pp. 2015. (Year: 2015).*

Webpage printout of https://en.wikipedia.org/wiki/Induced_cell_cycle_arrest, accessed Sep. 6, 2022, pp. 1-10. (Year: 2022).*

Webpage printout of https://www.aatbio.com/data-sets/prostanoid-ep3-receptor-inhibitors-ic50-ki, accessed Sep. 6, 2022, pp. 1-4. (Year: 2022).*

Rehman et al., Neurosurg Focus 2015 38(3), E14. (Year: 2015).*

Carlson et al., "Numerical stimulation of tumor treating fields effects on cell structures: Mechanism and signaling pathway candidates," Proceedings of the 110th Annual Meeting of the American Association for Cancer Research, Mar. 29-Apr. 3, 2019, Atlanta, Georgia, Abstract nr3725.

Diamant et al., "Evaluating the compatability of tumor treating electric fields with key anti-tumoral immune functions," Proceedings of the 110th Annual Meeting of the American Association for Cancer Research, Mar. 29-Apr. 3, 2019, Atlanta, Georgia, Abstract nr3954.

Giladi et al., "Tumor treating fields (TTFields) delay DNA damage repair following radiation treatment of glioma cells," Radiation Oncology, vol. 12, No. 206, pp. 1-13, 2017.

Giladi et al., "Tumor Treating Fields (TTFields) Delay DNA Damage Repair Following Radiation Treatment of Glioma Cells: Implications for Irradiation Through TTFields Transducer Arrays," International Journal of Radiation Oncology Biology Physics, vol. 99, Issue 2, p. S32, Oct. 2017.

International Search Report and Written Opinion issued in application No. PCT/IB2020/052959 dated Jul. 15, 2020.

Karanam et al., "Exploiting tumor treating fields induced downregulation of BRCA1 pathway for novel combination therapies," Proceedings of the 110th Annual Meeting of the American Association for Cancer Research, Mar. 29-Apr. 3, 2019, Abstract nr3939.

Karanam et al., "Newly identified role of tumor treating fields in DNA damage repair and replication stress pathways," Proceedings of the 109th Annual Meeting of the American Association for Cancer Research, Chicago, Illinois, Apr. 14-18, 2018, Abstract nr3217.

Karanam et al., "Tumor Treating Fields Elicit a Conditional Vulnerability in Non-Small Cell Lung Cancer Lines Through the Down-Regulation of Key DNA Repair and Replication Stress Pathways that When Targeted with Chemoradiation Results in Synergistic Cell Killing," International Journal of Radiation Onocology Biology Physics, vol. 102, No. 3, p. e184, Nov. 2018.

Karanam et al., "Tumor Treatment Fields downregulate specific transcription factors leading to reduced DNA repair capacity, increased replication stress, the inhibition of mitophagy and enhanced cell death," Neuro Onc., vol. 19, Suppl. 6, VI4-VI50, Nov. 2017.

Karanam et al., "Tumor treatment fields downregulate the BRCA1/FA pathway genes leading to reduced DNA repair capacity, the inhibition of mitophagy and enhanced cell death," Cancer Research, vol. 77, Suppl. 13, Abstract nr2138, 2017.

Kirson et al., "Alternating electric fields arrest cell proliferation in animal tumor models and human brain tumors," PNAS, vol. 104, No. 24, pp. 10152-10157, Jun. 2007.

Krex et al., "Efficacy of Tumor Treating Fields (TTFields) and Aurora B kinase inhibtor," Proceedings of the 109th Annual Meeting of the American Associate for Cancer Research, Apr. 14-18, 2018, Chicago, Illinois, Abstract nr1463.

Lavy et al., "Cancer cell lines response to tumor treating fields: results of a meta-analysis," Neruo. Onc., vol. 20, Suppl. 3, p. i282, Sep. 2018.

Morales et al., "Tumor treating fields (TTFields) significantly alters how tumor cells repair double stranded breaks using homeologous Alu sequences," Proceedings of the 110th Annual Meeting of the American Association for Cancer Research, Mar. 29-Apr. 3, 2019, Atlanta, Georgia, Abstract nr3493.

(56) References Cited

OTHER PUBLICATIONS

Rodriguez-Aguayo et al., "PTGER3 induces ovary tumorigenesis and confers resistance to cisplatin therapy through up-regulation Ras-MAPK/Erk-ETS1-ELK1/CFTR1 axis," EBioMedicine, vol. 40, pp. 290-304, Jan. 2019.

Schneiderman et al., "Tumor Treating Fields (TTFields) Inhibit Cancer Cell Migration and Invasion by Inducing Reorganization of the Actin Cytoskeleton and Formation of Cell Adhesions," Neuro. Onc., vol. 20, Suppl. 6, p. vi30, Nov. 2018.

Schneiderman et al., "Tumor Treating Fields affect invasion properties and cell morphology of various cancer cells," Neruo Onc., vol. 20, Suppl. 3, p. i282, Sep. 2018.

Shteingauz et al., "Induction of autophagy following TTFields application serves as a survival mechanism mediated by AMPK activation," Proceedings of the 109th Annual Meeting of the American Association for Cancer Research, Apr. 14-18, 2018, Chicago, Illinois, Abstract nr1343.

Slangen et al., "Cell cycle analysis during TTF to exploit novel targets for increasing treatment efficacy," Proceedings of the 110th Annual Meeting of the American Association for Cancer Research, Mar. 29-Apr. 3, 2019, Atlanta, Georgia, Abstract nr4419.

Story et al., "Exposure to Tumor Treating Fields Inhibits DNA Repair, Induces Replication Stress and Renders Tumor Cells Sensitive to Agents that Impinge Upon These Pathways," Neuro. Onc., vol. 20, Suppl. 6, p. vi30, Nov. 2018.

Tuszynski et al., "An Overview of Sub-Cellular Mechanisms Involved in the Action of TTFields," International Journal of Environmental Research and Public Health, vol. 13, p. 1128, 2016.

Wong et al., "Dexamethasone exerts profound immunologic interference on treatment efficacy for recurrent glioblastoma," British Journal of Cancer, vol. 113, pp. 232-241, Jul. 2015.

Wong et al., "Tumor treating fields exert cellular and immunologic effects," Proceedings of the 109th Annual Meeting of the American Association for Cancer Research, Apr. 14-18, 2018, Chicago, Illinois, Abstract nr1707.

European Search Report issued in application No. EP21208102 dated Mar. 4, 2022.

Nakamura, "Cyclooxygenase (COS)-2 selective inhibitors: aspirin, a due COX-1/COX-2 inhibitor to COS-2 Selective Inhibitors," Nippon Yakurigaku Zassi, Folia Pharmacol. Jpn., vol. 118, pp. 219-230, 2001.

Wong et al., "Evidence for Improved Patient Outcomes with Adjuvant Celecoxib in Recurrent Glioblastoma Patients Treated with Tumor Treating Fields," Annals of Neurology, vol. 84, Suppl. 22, p. S124, Abstract S297, 2018.

* cited by examiner

FIG. 7A nSCORE rank

| GENE | ALL_1w | ALL_5w | LN428_1w | LN428_5w | LN827_1w | LN827_5w | U87_1w | U87_5w |
|---|---|---|---|---|---|---|---|---|
| FLI1 | 73 | 1 | 50 | 25 | 2094 | 2094 | 2094 | 6 |
| EHF | 2 | 2 | 7 | 5 | 2094 | 199 | 150 | 30 |
| ELF3 | 28 | 3 | 23 | 2 | 2094 | 2094 | 196 | 23 |
| PTGER3 | 121 | 4 | 1 | 1 | 145 | 1 | 17 | 8 |
| WWC1 | 2094 | 5 | 2094 | 2094 | 2094 | 2094 | 2094 | 13 |
| SLC2A4RG | 13 | 6 | 2094 | 2094 | 2094 | 15 | 2094 | 11 |
| FOXF1 | 107 | 7 | 71 | 467 | 1830 | 12 | 2094 | 88 |
| NFKBIZ | 32 | 8 | 2094 | 155 | 2094 | 2094 | 14 | 40 |
| ZNF488 | 11 | 9 | 2094 | 2094 | 2094 | 2094 | 14 | 7 |
| ZNF91 | 232 | 10 | 343 | 100 | 2094 | 2094 | 2094 | 64 |

PTGER3-dependent resistance:
Selection of Preexisting Resistant Cells vs. Network Remodeling

nSCORE rank

| GENE | ALL_6h | ALL_24h | LN428_6h | LN428_24h | LN827_6h | LN827_24h | U87_6h | U87_24h |
|---|---|---|---|---|---|---|---|---|
| PTGER3 | 6562 | 22 | 31 | 5 | 1477 | 8 | 112 | 14 |

PTGER3 pathway is enforced within 24h of TTFields
(favoring the Network Remodeling model over Selection)
(SEE NEXT SLIDE OR DETAILED EP3 SUBNETWORK)

METHODS FOR RESTORING SENSITIVITY TO TTFIELDS IN TTFIELDS-RESISTANT CANCER CELLS WITH PTGER3 INHIBITORS

CROSS REFERENCE TO RELATED APPLICATIONS

This Application claims the benefit of U.S. Provisional Application 62/826,078 (filed Mar. 29, 2019), and 62/849,535 (filed May 17, 2019), each of which is incorporated herein by reference in its entirety. All patents, patent applications, and publications cited herein are incorporated by reference in their entirety.

BACKGROUND

Tumor Treating Fields (TTFields) are an effective antineoplastic treatment modality delivered via non-invasive application of low intensity, intermediate frequency (e.g., 100-500 kHz), alternating electric fields. TTFields exert directional forces on polar microtubules and interfere with the normal assembly of the mitotic spindle. Such interference with microtubule dynamics results in abnormal spindle formation and subsequent mitotic arrest or delay. Cells can die while in mitotic arrest or progress to cell division leading to the formation of either normal or abnormal aneuploid progeny. The formation of tetraploid cells can occur either due to mitotic exit through slippage or can occur during improper cell division. Abnormal daughter cells can die in the subsequent interphase, can undergo a permanent arrest, or can proliferate through additional mitosis where they will be subjected to further TTFields assault. Giladi M et al. *Sci Rep.* 2015; 5:18046.

In the in vivo context, TTFields therapy can be delivered using a wearable and portable device (Optune®). The delivery system includes an electric field generator, 4 adhesive patches (non-invasive, insulated transducer arrays), rechargeable batteries and a carrying case. The transducer arrays are applied to the skin and are connected to the device and battery. The therapy is designed to be worn for as many hours as possible throughout the day and night.

In the preclinical setting, TTFields can be applied in vitro using, for example, the Inovitro™ TTFields lab bench system. Inovitro™ includes a TTFields generator and base plate containing 8 ceramic dishes per plate. Cells are plated on a cover slips placed inside each dish. TTFields are applied using two perpendicular pairs of transducer arrays insulated by a high dielectric constant ceramic in each dish. The orientation of the TTFields in each dish is switched 90° every 1 second, thus covering different orientation axes of cell divisions.

Glioblastoma (GBM) is the most common and deadliest malignant brain cancer in adults despite surgery and aggressive chemoradiotherapy. Tumor Treating Fields (TTFields) have been approved in combination with adjuvant temozolomide chemotherapy for newly diagnosed GBM. The addition of TTFields resulted in a significant improvement in overall survival. TTFields are low-intensity alternating electric fields that are thought to disturb mitotic macromolecules' assembly, leading to disrupted chromosomal segregation and cell death. However, treatment resistance develops in many TTFields responders.

Several human GBM cell lines were developed that demonstrated relative resistance to the cytotoxic effects of TTFields compared to the parental cells.

SUMMARY

Methods of reducing viability of TTFields-resistant cancer cells in a subject by recommending administering a Prostaglandin E Receptor 3 (PTGER3) inhibitor to the subject, and applying an alternating electric field to the cancer cells of the subject are provided. The alternating electric field has a frequency between 100 and 500 kHz.

In some instances, methods of preventing cancer cells of a subject from developing resistance to alternating electric fields by recommending administering a PTGER3 inhibitor to the subject, and applying an alternating electric field to the cancer cells of the subject are provided. The alternating electric field has a frequency between 100 and 500 kHz.

In some instances, methods of restoring sensitivity to TTFields in TTFields-resistant cancer cells of a subject by recommending administering a PTGER3 inhibitor to the subject are provided. In this aspect, sensitivity to TTFields in the TTFields-resistant cancer calls of the subject is substantially restored.

In some instances, methods of preventing cancer cells of a subject from developing resistance to alternating electric fields by prescribing a PTGER3 inhibitor for the subject and applying an alternating electric field to the cancer cells are provided. The alternating electric field has a frequency between 100 and 500 kHz.

In some instances, methods of restoring sensitivity to TTFields in TTFields-resistant cancer cells of a subject by prescribing a PTGER3 inhibitor for the subject. In this aspect, sensitivity of the TTFields-resistant cancer cells of the subject to TTFields is restored after the PTGER3 inhibitor is administered to the subject.

In some instances, methods of reducing viability of TTFields-resistant cancer cells in a subject by recommending administering an inhibitor of a target in the EP3-controlled resistance pathway to the subject, and applying an alternating electric field to the cancer cells of the subject are provided. The alternating electric field has a frequency between 100 and 500 kHz.

BRIEF DESCRIPTION OF DRAWINGS

FIGS. 7A-7B show that PTGER3 is the top ranked master regulator of resistance, across all three GBM TTFields-resistant cell lines

DETAILED DESCRIPTION

Figure 1A:
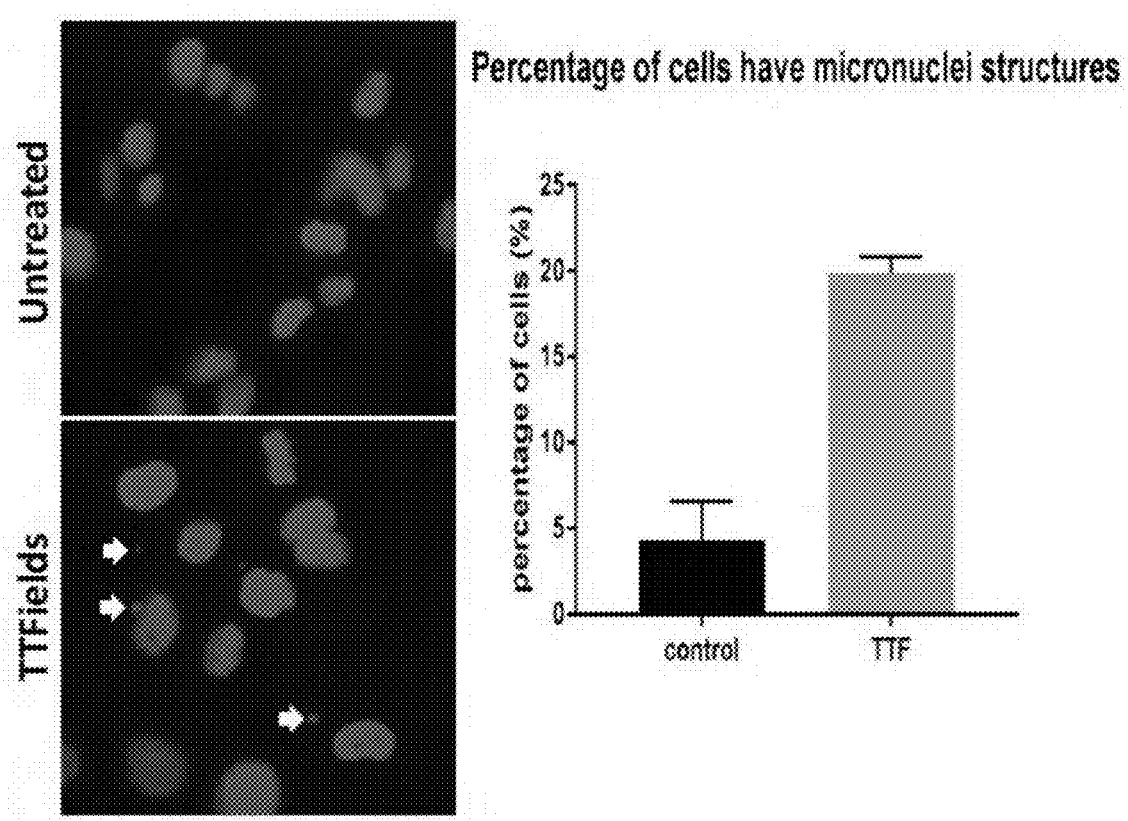
FIG. 1A shows an example of development of micronuclei in human LN827 glioblastoma (GBM) cell lines, comparing TTFields untreated cells and TTFields treated cells (left panel) and showing the percentage of cells having micronuclei structures (bar graph, right panel)

TTFields are an effective anti-neoplastic treatment modality delivered via non-invasive application of low intensity, intermediate frequency (e.g., 100-500 kHz), alternating electric fields. However, in certain circumstances, tumor cells can develop resistance to TTFields treatment leading to a reduction in efficacy in these circumstances. In some aspects, resistance to TTFields is termed an increase in "stemness" or a phenotype similar to stem cells. Stemness can be measured by expression of stemness markers such as CD44 and by the ability to grow in serum-free media in 3D spheres and to form brain tumors when implanted into the brain of immunosuppressed mice.

Importantly, TTFields-induced chromosomal instability such as the formation of cytoplasmic micronuclei was preserved in resistant cells compared to their sensitive counterparts, indicating resistance to TTFields is mediated through a non-biophysical mechanism. Indeed, TTFields-induced inflammatory response was severely suppressed in resistant cells, supporting the hypothesis that that resistance to TTFields is conferred by a selective loss of the deleterious effects induced by the biophysical insults. This acquired TTFields resistance phenotype was associated with a transition to a stem-like state as determined by a standard neurosphere assay.

Recently, the immune sensing molecule cyclic GMP-AMP synthase (cGAS)-Stimulator of Interferon Genes (STING, encoded by TMEM 173) pathway was identified as an important component of cytosolic DNA sensing and plays an important role in mediating the immune response in cells. Ghaffari et al., British Journal of Cancer, volume 119, pages 440-449 (2018); see, e.g., FIG. 3. Activation of the STING pathway mediates the immune response by responding to abnormalities in the cells (e.g., the presence of cytoplasmic double-stranded DNA (dsDNA)).

Prostaglandin E receptor 3 (PTGER3) is a G-protein coupled receptor and one of four receptors for prostaglandin E2. PTGER3 is implicated in biological systems and diseases related to inflammation, cancer, digestion, the nervous system, kidney function, blood pressure, and uterine contraction.

PTGER3 inhibitors include NSAID (e.g., aspirin, ibuprofen), cox2 inhibitor (e.g., celecoxib, valdecoxib, rofecoxib), L798,106, and DG041. NSAIDs are common over-the-counter medications used for pain relief and reducing inflammation.

Aspects described herein used a systems approach, aided by a suite of innovative computational platforms, to understand "stemness" development in resistant cells and identify master regulators of the resistance mechanism. Three networks were found disrupted, including nervous system developmental regulation, inflammatory response and cell-cell adhesion, all of which play roles in GBM stem-like cells.

Utilizing a unique master regulator ranking system, the Prostaglandin E Receptor 3 (PTGER3) was identified as a key master regulator at the apex of these pathways and responsible for the TTFields-resistant phenotype. PTGER3 is rapidly upregulated in GBM cells when exposed to TTFields, and channels treated cells away from the beneficial inflammatory pathways that TTFields also activates in parallel.

The PTGER3 signal transduction pathway is upregulated via interaction with Prostaglandin E2 (PGE2). Combination of TTFields and aspirin or other traditional NSAIDs (e.g., cox2 inhibitors) can prevent PGE2 biosynthesis and therefore the activation of PTGER3 signaling. Alternatively, PTGER3 receptor antagonists (e.g. L798,106,106, ONO-AE3-240, and DG-O41) can be used along or in combination with other PTGER3 antagonists and inhibitors. Such combinations can be used restore the sensitivity to TTFields in cells that developed resistance.

In addition, GBM cells treated with a PTGER3 inhibitor while exposed to TTFields can prevent the cells from developing resistance to TTFields, for example, from about 3 weeks later to greater than 5 weeks later.

Methods of reducing viability of TTFields-resistant cancer cells in a subject by recommending administering a Prostaglandin E Receptor 3 (PTGER3) inhibitor to the subject, and applying an alternating electric field to the cancer cells of the subject are provided. The alternating electric field can have a frequency between 100 and 500 kHz.

The term "reducing viability," as used herein, refers to decreasing proliferation, inducing apoptosis, or killing cancer cells. The term "TTFields-resistant cancer cells," as used herein, refers to cancer cells showing a 10, 20, 30, 40, 50, 60, 70, 80, 90, or 100% reduction in sensitivity to TTFields treatment compared to TTFields-sensitive cancer cells. The term "sensitivity," as used herein, refers responsiveness to TTFields treatment as measured by, for example, a reduction in cell number following treatment with TTFields.

The term "recommending" refers to a suggestion or instruction from, for example, a medical professional such as a doctor, physician assistant, nurse, nurse practitioner, etc., to a subject such as a patient.

In some instances, the PTGER3 inhibitor is selected from the group consisting of one or more of an NSAID (e.g., aspirin, ibuprofen), cox2 inhibitor (e.g., celecoxib, valdecoxib, rofecoxib), L798,106, and DG041. In one aspect, the PTGER3 inhibitor is aspirin.

In some instances, a recommended concentration of the PTGER3 inhibitor in the subject is from about 1 to 500 nanomolar for L798,106, 0.1 to 2 millimolar for aspirin, 0.5 to 50 nanomolar for DG041, or 1 to 500 nanomolar for celecoxib. The term "recommended concentration" can refer to a recommended dose sufficient to provide intermittent or sustained level of a PTGER3 inhibitor in a subject. In some instances, the recommended concentration of the PTGER3 inhibitor in the subject is maintained for at least about 3 days to 5 weeks. In some instances, the cancer cells are selected from glioblastoma, lung cancer, pancreatic cancer, mesothelioma, ovarian cancer, and breast cancer cells.

Further aspects provide methods of preventing cancer cells of a subject from developing resistance to alternating electric fields, by recommending administering a Prostaglandin E Receptor 3 inhibitor to the subject and applying an alternating electric field to the cancer cells of the subject. The alternating electric field having a frequency between 100 and 500 kHz. In some instances, the alternating electric field has a frequency between 100 and 300 kHz.

In some instances, the PTGER3 inhibitor is selected from the group consisting of one or more of an NSAID (e.g., aspirin, ibuprofen), cox2 inhibitor (e.g., celecoxib, valdecoxib, rofecoxib), L798,106, and DG041. In one aspect, the PTGER3 inhibitor is aspirin.

In some instances, a recommended concentration of the PTGER3 inhibitor in the subject is from about 1 to 500 nanomolar for L798,106, 0.1 to 2 millimolar for aspirin, 0.5 to 50 nanomolar for DG041, or 1 to 500 nanomolar for celecoxib. The term "recommended concentration" can refer to a recommended dose sufficient to provide intermittent or sustained level of a PTGER3 inhibitor in a subject. In some instances, the recommended concentration of the PTGER3 inhibitor in the subject is maintained for at least about 3 days to 5 weeks. In some instances, the cancer cells are selected from glioblastoma, lung cancer, pancreatic cancer, mesothelioma, ovarian cancer, and breast cancer cells.

Further aspects provide methods of restoring sensitivity to TTFields in TTFields-resistant cancer cells of a subject by recommending administering a PTGER3 inhibitor to the subject, wherein sensitivity to TTFields is substantially restored in the TTFields-resistant cancer calls of the subject.

The term "restoring sensitivity" refers to re-establishing the responsiveness of TTFields-resistant cells to the responsiveness of the TTFields-sensitive cells. In this aspect, "responsiveness" is measured by counting the number of cells before and after exposure to TTFields. The term "substantially restored" refers to increasing the responsiveness of TTFields-resistant cells. In some instances, the responsiveness of TTFields-resistant cells is restored by at least 10%. In some instances, the responsiveness of TTFields-resistant cells is restored by at least 25%. In some instances, the responsiveness of TTFields-resistant cells is restored by at least 50%.

In some instances, the PTGER3 inhibitor is selected from the group consisting of one or more of an NSAID (e.g., aspirin, ibuprofen), cox2 inhibitor (e.g., celecoxib, valdecoxib, rofecoxib), L798,106, and DG041. In one aspect, the PTGER3 inhibitor is aspirin.

In some instances, a recommended concentration of the PTGER3 inhibitor in the subject is from about 1 to 500 nanomolar for L798,106, 0.1 to 2 millimolar for aspirin, 0.5 to 50 nanomolar for DG041, or 1 to 500 nanomolar for celecoxib. The term "recommended concentration" can refer to a recommended dose sufficient to provide intermittent or sustained level of a PTGER3 inhibitor in a subject. In some instances, the recommended concentration of the PTGER3 inhibitor in the subject is maintained for at least about 3 days to 5 weeks. In some instances, the cancer cells are glioblastoma cells.

Yet another aspect provides methods of reducing viability of TTFields-resistant cancer cells in a subject, the method by prescribing a PTGER3 inhibitor to the subject, and applying an alternating electric field to the cancer cells. The alternating electric field can have a frequency between 100 and 500 kHz.

The term "prescribing," as used herein, refers to a medical professional authorized to write a prescription providing a prescription for a drug to a subject or communicating a prescription to a pharmacy or other medicinal dispensary.

Further aspects provide methods of preventing cancer cells of a subject from developing resistance to alternating electric fields by prescribing a PTGER3 inhibitor for the subject, and applying an alternating electric field to the cancer cells. The alternating electric field can have a frequency between 100 and 500 kHz.

Yet another aspect provides methods of restoring sensitivity to TTFields in TTFields-resistant cancer cells of a subject by prescribing a PTGER3 inhibitor for the subject wherein sensitivity of the TTFields-resistant cancer cells of the subject to TTFields is restored after the PTGER3 inhibitor is administered to the subject.

In some instances, methods of reducing viability of TTFields-resistant cancer cells in a subject by recommending administering an inhibitor of a target in the EP3-controlled resistance pathway to the subject, and applying an alternating electric field to the cancer cells of the subject are provided. The alternating electric field has a frequency between 100 and 500 kHz.

In some instances, the target in the EP3-controlled resistance pathway is selected from the group consisting of ZNF488 and PRDM8. Examples of inhibitors of PRDM8 include, but are not limited to, azacytidine and decitabine.

As shown in FIG. 1A, Human LN827 glioblastoma cells were treated by TTFields for 24 hours at 200 kHz then fixed by 4% PFA for 20 min. DAPI (4',6-diamidino-2-phenylindole) was used to stain the cells at a dilution of 1:5000 and incubated for 5 min at room temperature staining for nuclear and micronuclei. Micronuclei can be seen (arrows) in the TTFields treated cells (bottom panel). The bar graph shows about a 15% increase in micronuclei structures.

Figure 1B:
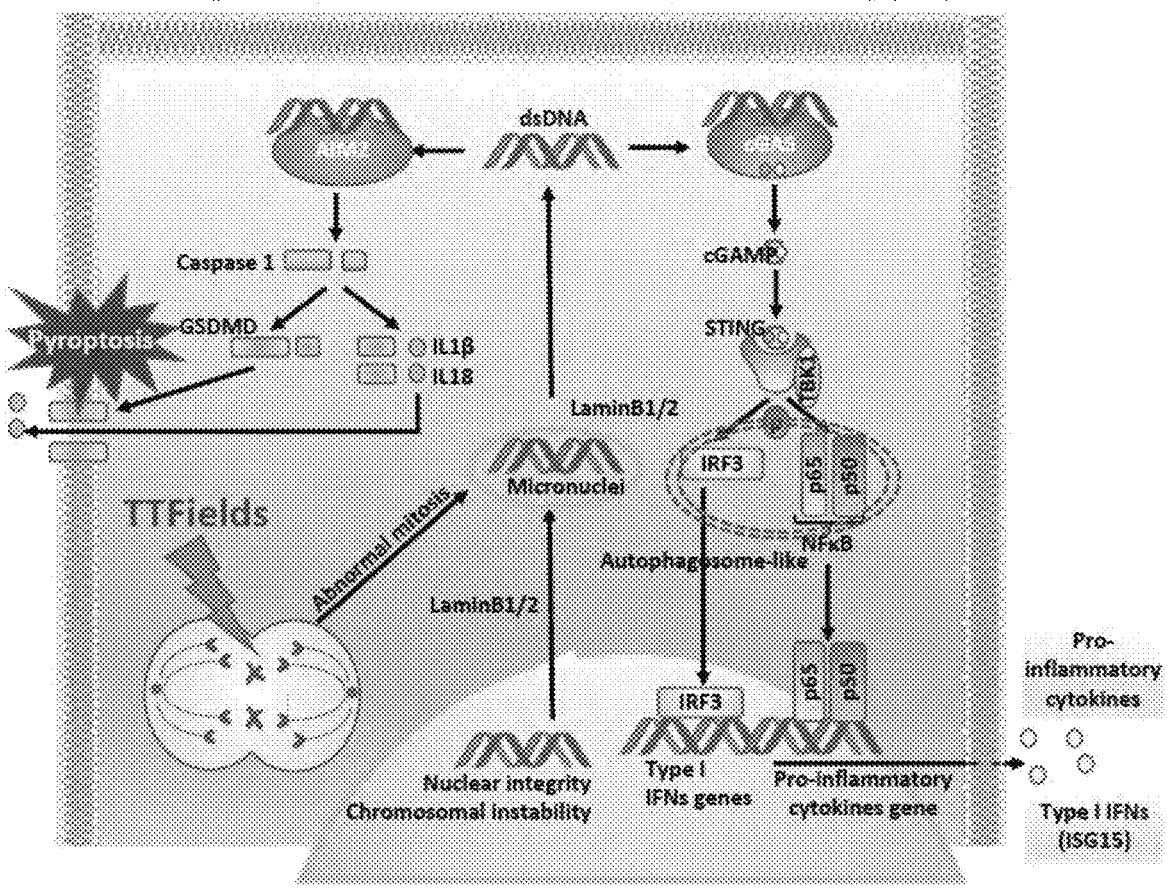
FIG. 1B provides an exemplary schematic showing how TTFields-generated micronuclei induce the STING pathway and pyroptosis leading to abnormal mitosis, chromosomal instability, and generation of pro-inflammatory cytokines and type I interferons.

FIG. 1B depicts induction of the proinflammatory STING and pyroptosis pathways by dsDNA (double-stranded DNA). dsDNA can be produced from micronuclei induced by abnormal mitosis. Abnormal mitosis can be induced, for example, by TTFields. TTFields can also reduce nuclear envelope integrity as shown by disruption of lamin B1 structures leading to dsDNA in the cytoplasm and induction of the STING pathway as shown.

Figure 2:
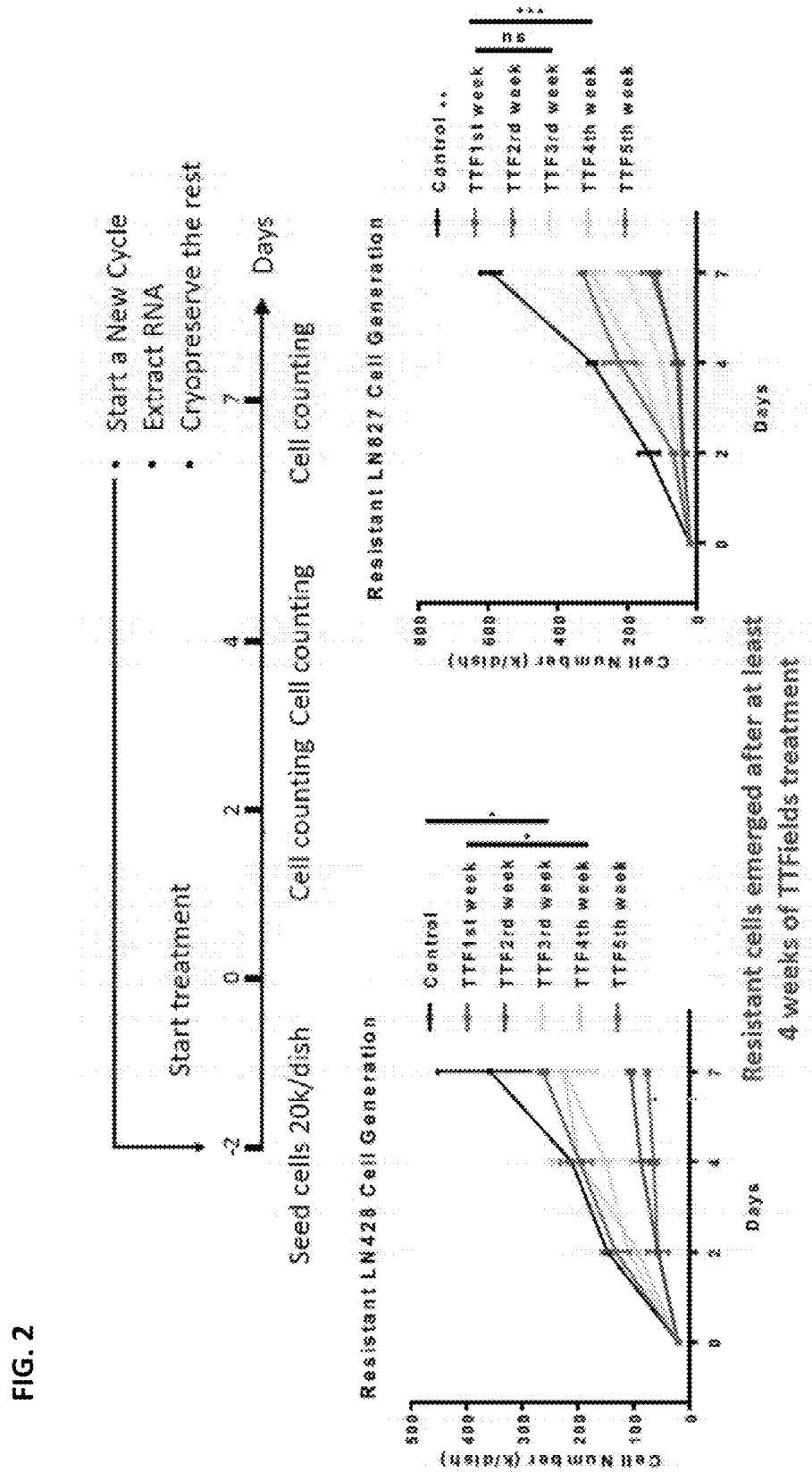
FIG. 2 shows an exemplary procedure for development of TTFields-resistant glioblastoma cells with increased resistance to TTFields indicated by an increase in cell number.

For the experiments summarized in FIG. 2, TTFields-resistant human GBM cell lines were generated by seeding LN827 cells at a density of 10,000/ml and treated with TTFields for in repeated 1-week cycles at a frequency of 200 kHz. For each cycle, cells were counted on day 2, day 4 and day 7. At the end of each cycle, the cells were re-seeded at the same density as on day 0, harvested and processed for RNAseq and cryopreservation for future analysis. Resistant cells emerged after at least four weeks of TTFields treatment. As shown in FIG. 2, cell numbers are significantly higher in TTFields-treated cells after the fifth week compared to preceding weeks demonstrating development of cells resistant to cell number-reducing effects of TTFields in non-resistant cells.

Figure 3:
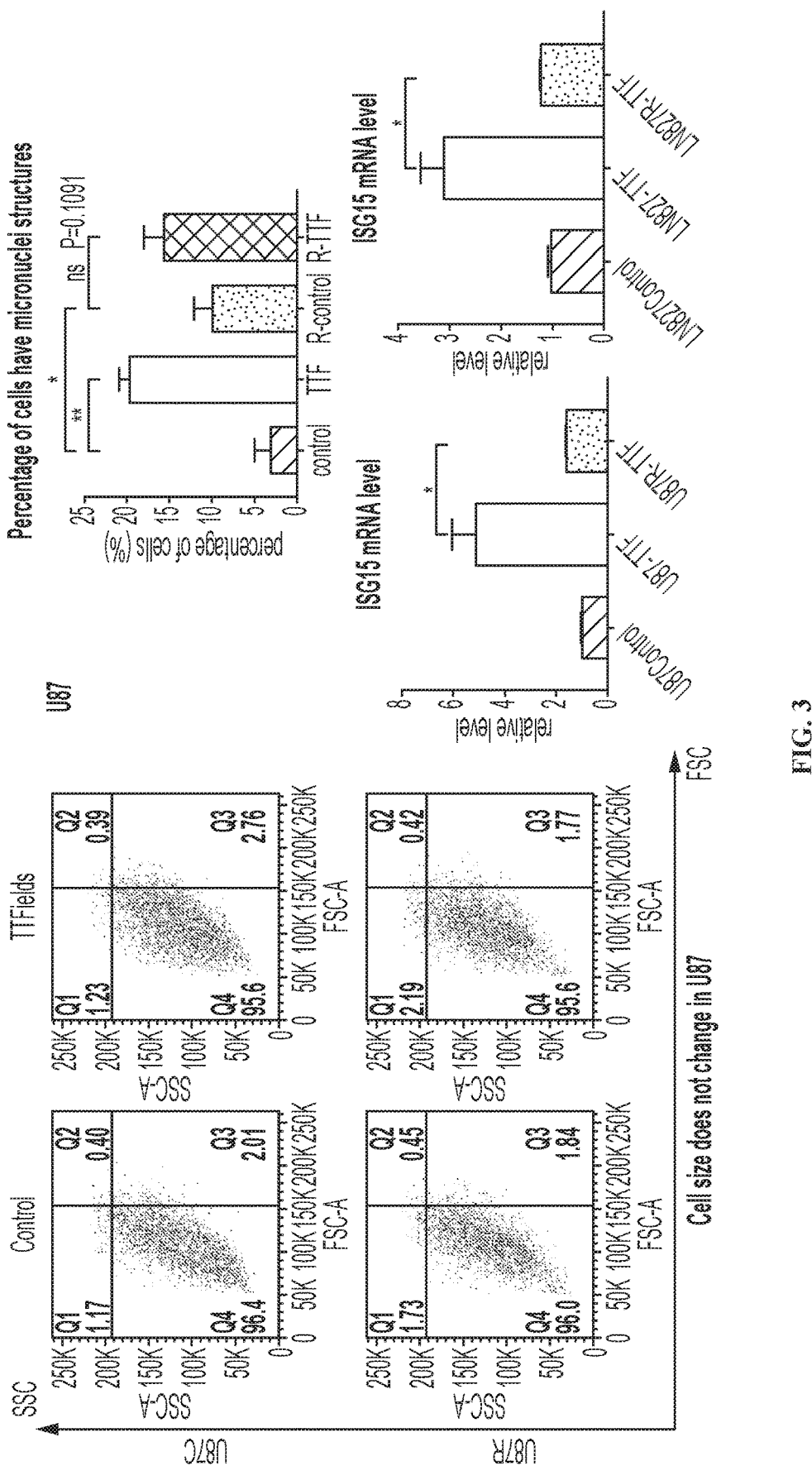
FIG. 3 shows the results of an exemplary experiment demonstrating that U87 GBM resistant cells cell size does not change, and the cells form micronuclei in response to TTFields, but no longer generate the STING pathway pro-inflammatory cytokine response.

Human GBM cell lines were treated with and without TTFields for 1 week (TTF=sensitive cells; R-TTF=resistant cells) at a frequency of 200 kHz (FIG. 3). Cells were analyzed for size (flow cytometry), micronuclei structures (immunofluorescence), and type 1 interferon response genes (qPCR). As shown in the left panel, U87C (sensitive) and U87R (resistant) did not show a change in cell size. However, the right panel (top) shows that micronuclei are still formed (compare TTF and R-TTF). Interferon-stimulated gene 15 (ISG15), a key type 1 interferon response gene, is no longer generated in U87R and LN827R resistant cell lines.

Figure 4:
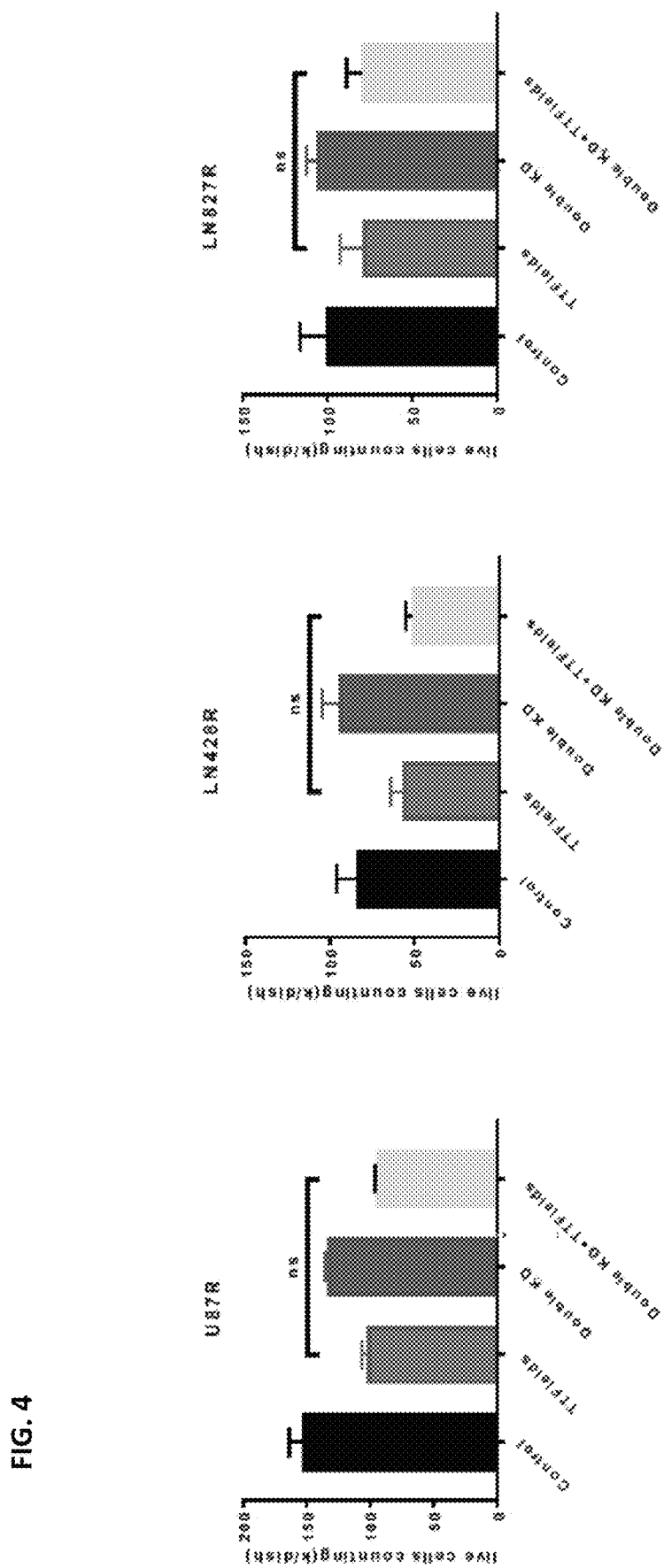
FIG. 4 shows that TTFields-resistant GBM Cells (U87R, LN428R, and LN827R) maintain a resistant phenotype when depleted of STING and AIM.

FIG. 4 shows that the proinflammatory pathways and the resistance pathways induced by TTFields are independent. The STING/AIM2 pathways were depleted in "knock down" (KD) TTFields-resistant cell lines (U87R, LN428R, LN827R) using shRNA (short hairpin RNA). Cells were treated as indicated for 3 days and cell numbers were determined by cell counter (Bio-Rad TC10). As shown in FIG. 4, resistance to TTFields is maintained even when the STING/AIM2 pathways are inhibited by shRNA (e.g., compare TTFields bar to double-KD+TTFields).

Figure 5:
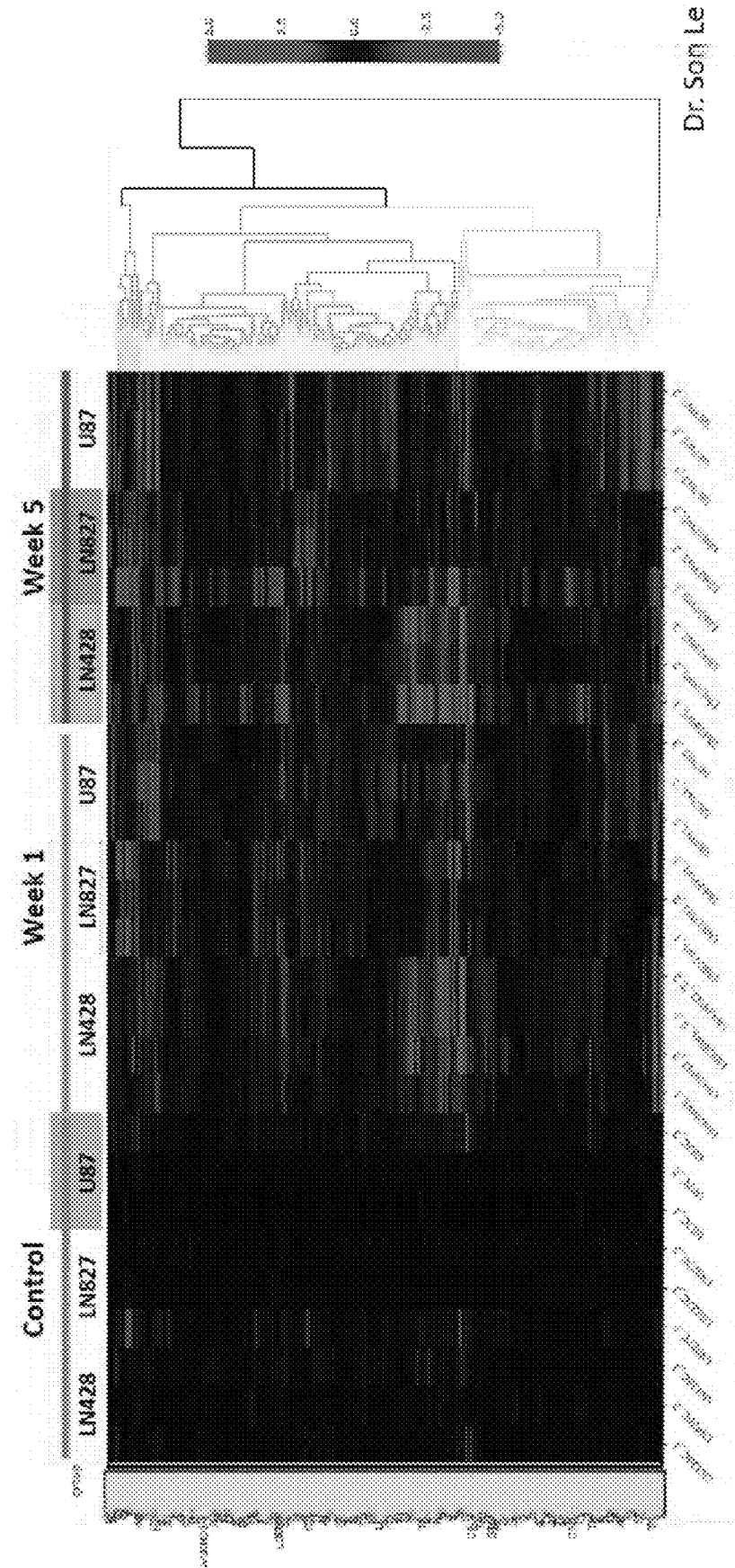
FIGS. 5 and 6 show an exemplary change in global network gene expression using NETZEN, a proprietary AI Algorithm, in resistant GBM cells soon after TTFields exposure.

FIG. 5 shows the exemplary change in global gene expression changes in resistant cells in control cells, and one week and five weeks after TTFields exposure in resistant cells (LN428, LN827, and U87).

Figure 6:
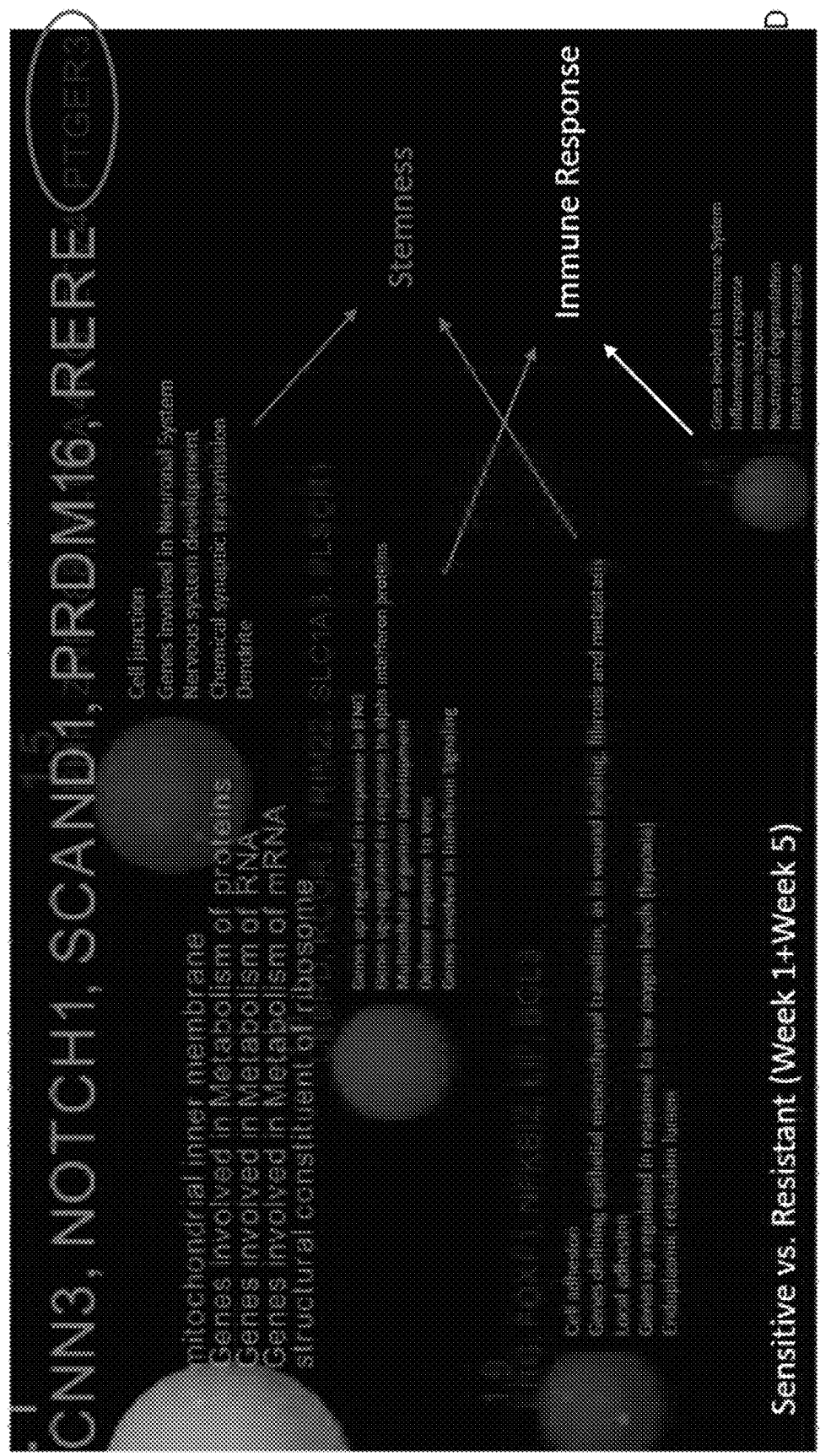

FIG. 6 shows global gene network changes in resistant GBM cells using an algorithm and the association of identified genes with phenotypes associated with sternness (e.g. ERG, FOXF1, NFKBIZ, LIF, BCL3, EHF, ZNF488, SLC2A4RG, ETV4, PTGER3) and immune response (e.g. CEBPD, RCOR2, TRIM22, SLC1A3, PLSCR1, FLI1).

Figure 7B:
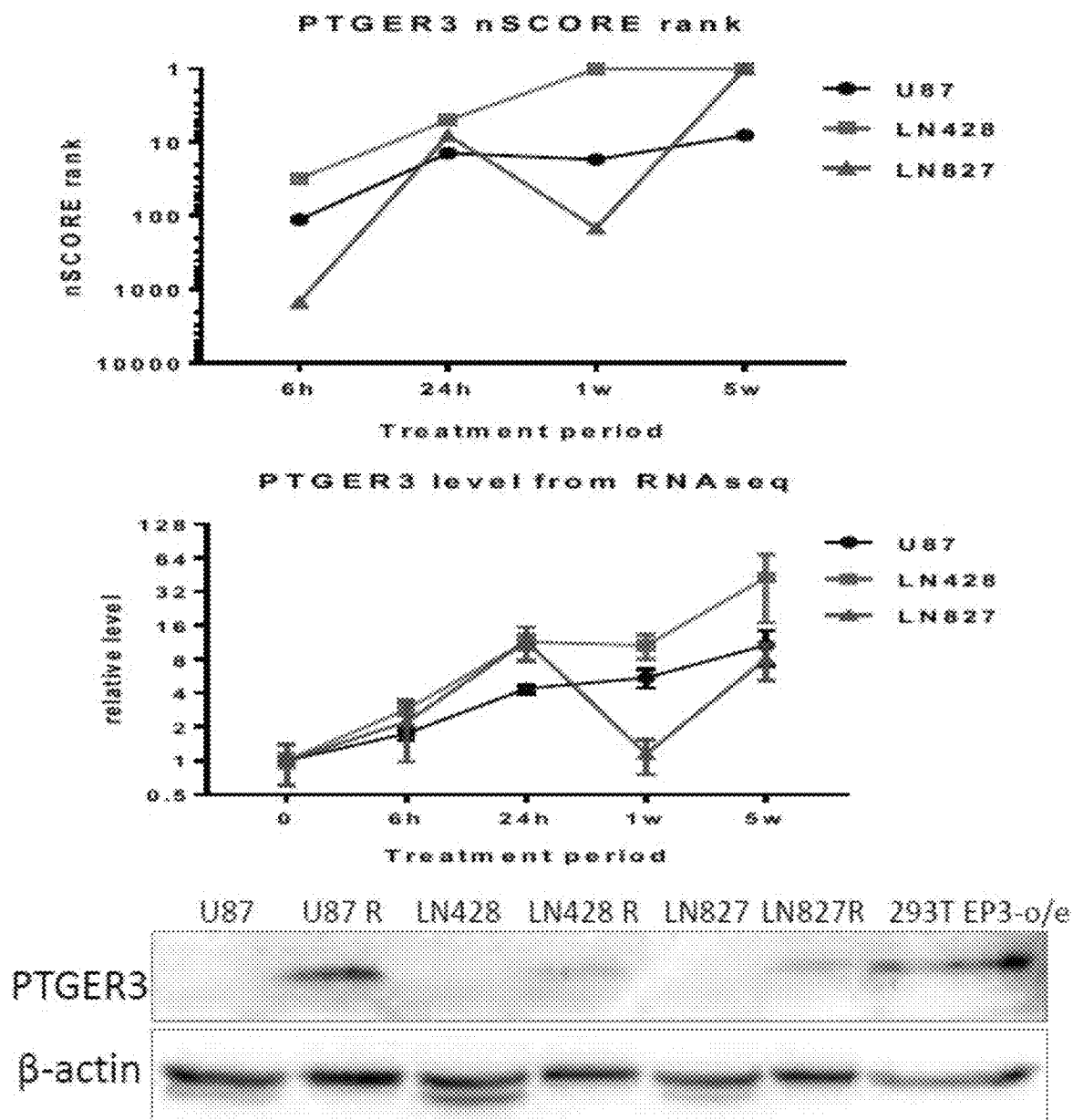

FIG. 7A shows the nSCORE rank for the top ranked master regulator of resistance to TTFields identified using NETZEN (FIG. 7A) across 4 different time points (0 hour, 6 hours, 24 hours, 1 week, 5 weeks) in 3 different GBM cell lines. FIG. 7B shows PTGER3 expression determined RNAseq and Western blotting correlates to PTGER3 nSCORE rank. EP3 overexpression in 293T cell line serves as a positive control, and B-actin as loading controls.

Figure 8:
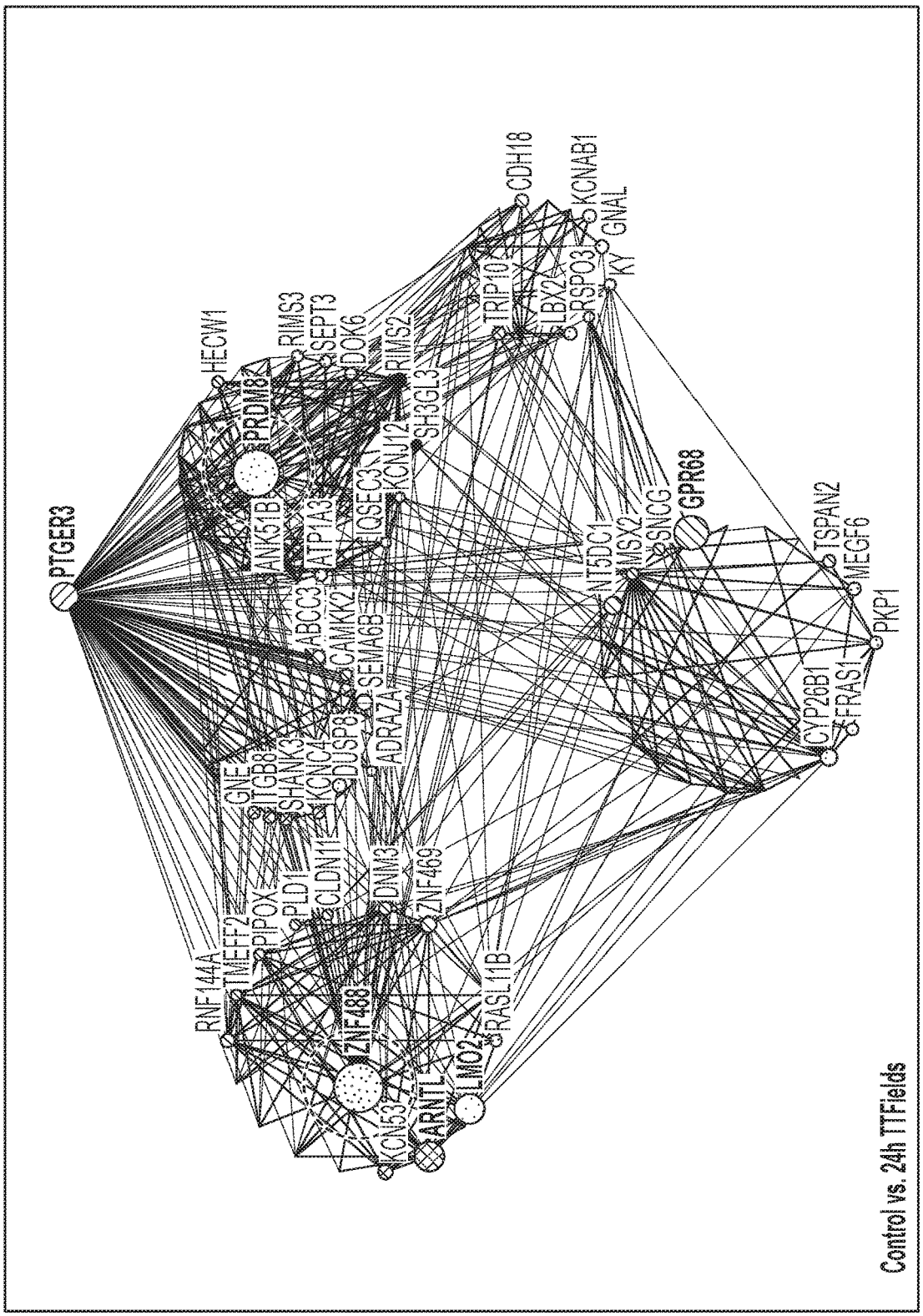
FIG. 8 shows an exemplary 2D view of the core PTGER3 subnetwork in TTFields-resistant cells after 24 hours of TTFields treatment.
Figure 9:
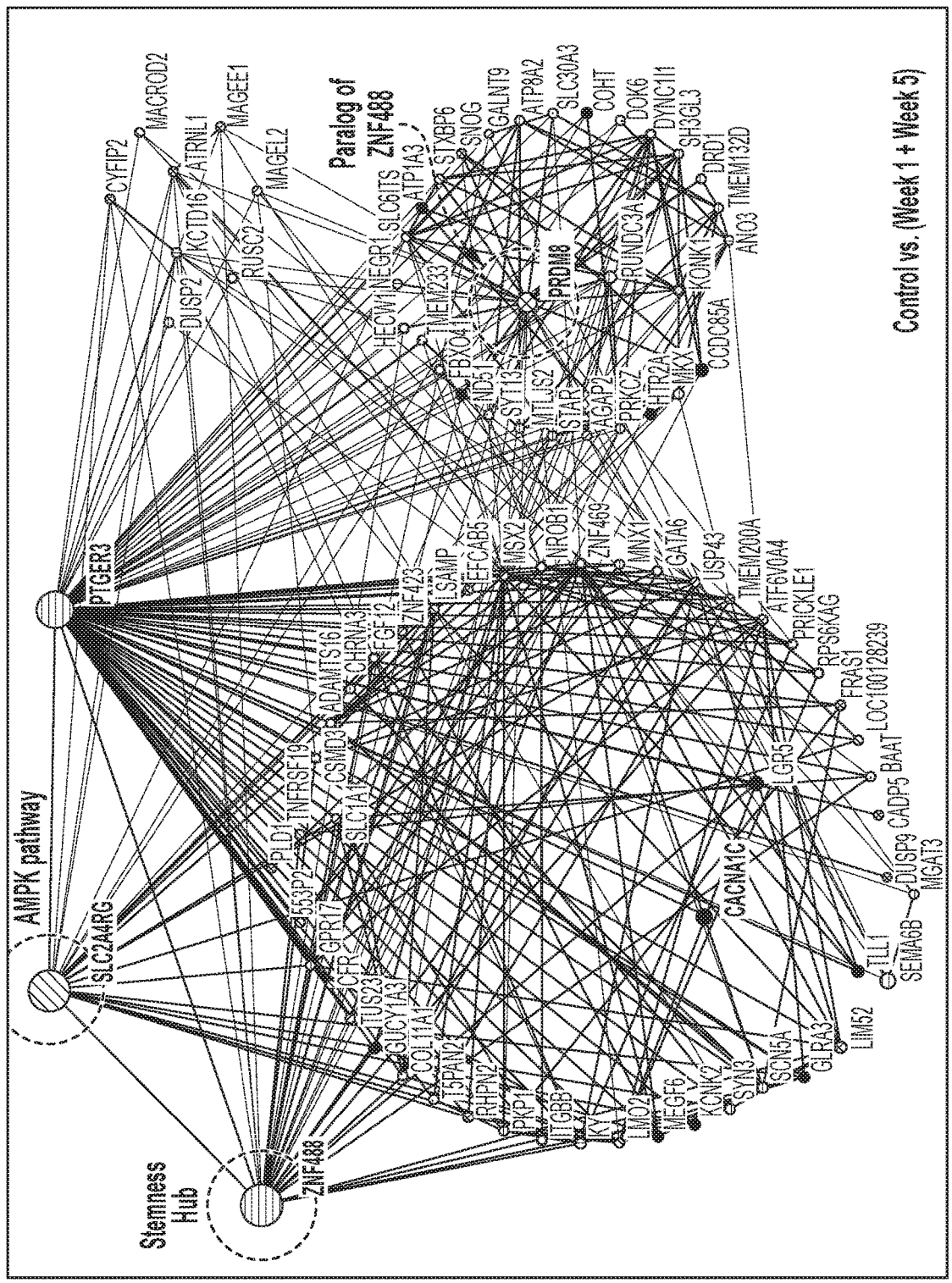
FIG. 9 shows an exemplary 2D of the core PTGER3 subnetwork in TTFields-resistant cells after one and five weeks.

FIG. 8 provides a two-dimensional view of the gene subnetwork controlled by PTGER3 24 hours after exposure to TTFields. FIG. 9 shows how the PTGER3 controlled gene subnetwork become dominant as resistant cells take over the cell culture (week 1+week 5).

Figure 10:
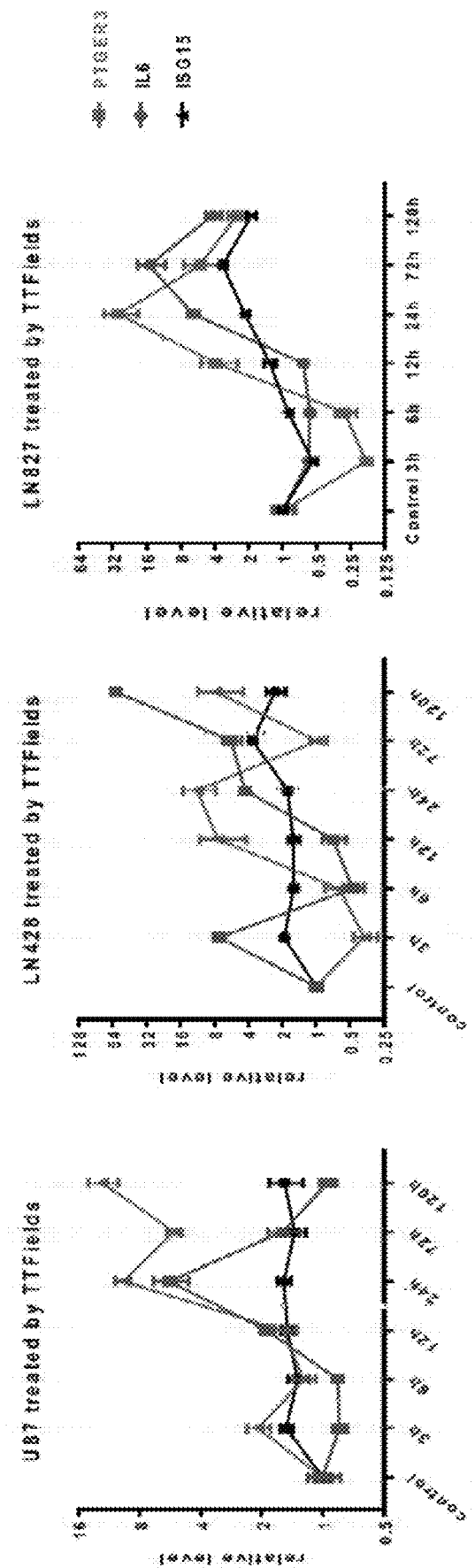
FIG. 10 shows that PTGER3 upregulation correlates with TTFields-induced STING and Pyroptosis activation in initial exposure to TTFields in three GBM cell lines using quantitative PCR.

FIG. 10 shows that PTGER3 upregulation correlates with TTFields-induced STING and Pyroptosis activation following exposure to TTFields in three. Quantitative-RT-PCR was utilized to detect the transcriptional levels of PTGER3, IL6 and ISG15 (markers for STING and Pyroptosis activation).

Figure 11:
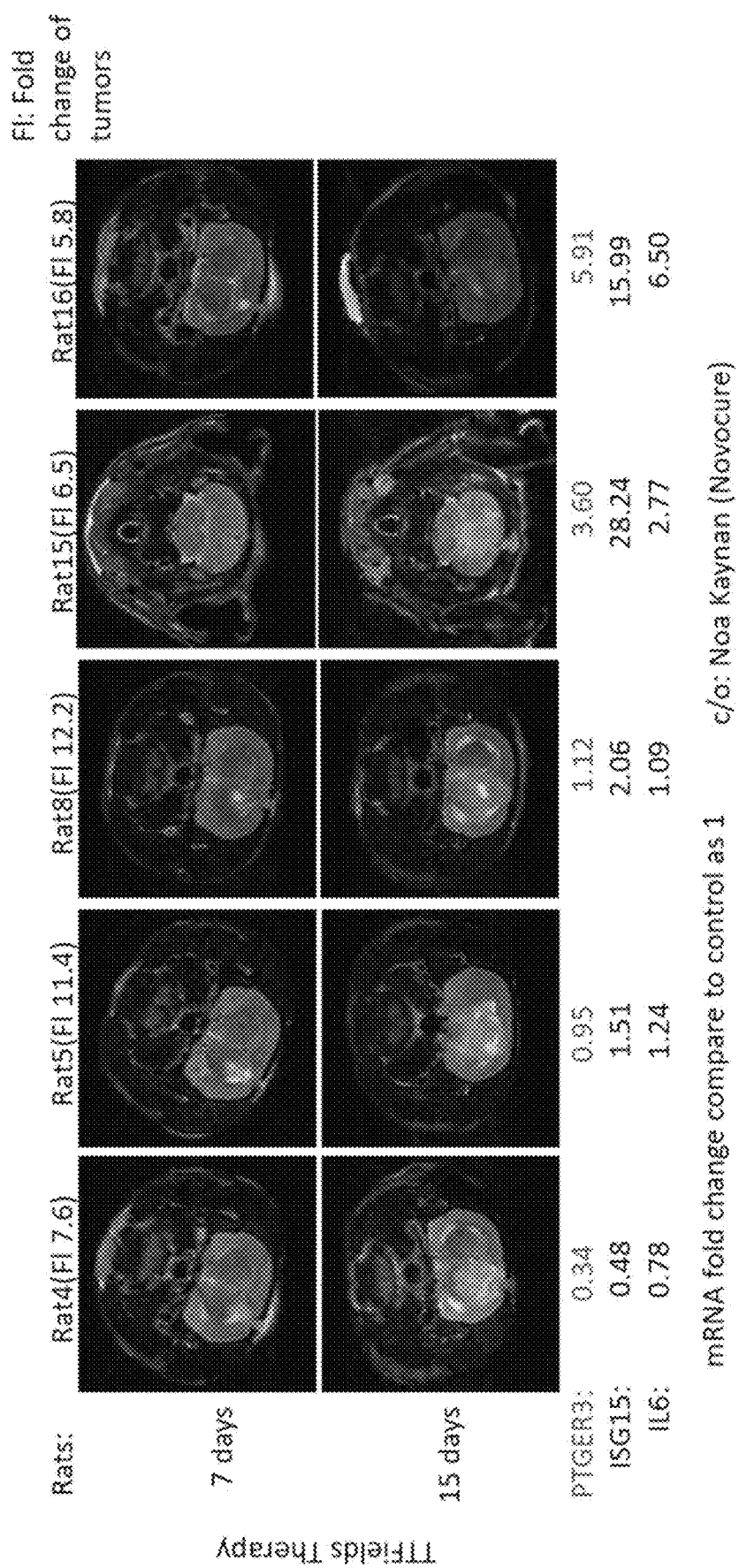
FIG. 11 shows that PTGER3 upregulation correlates with TTFields-induced STING proinflammatory cytokines in a rat GBM model.

FIG. 11 shows that PTGER3 upregulation correlates with TTFields-induced STING proinflammatory cytokines in vivo in a rat GBM models. was established by Novocure. TTFields treatment was started in an F98 rat orthotopic GBM model (Novocure) 1 week after injection and lasted for 1 week. Animals were then euthanized, and tumors collected for RNA. Quantitative-RT-PCR was performed to detect the transcriptional levels of PTGER3, IL6 and ISG15.

Figure 12:
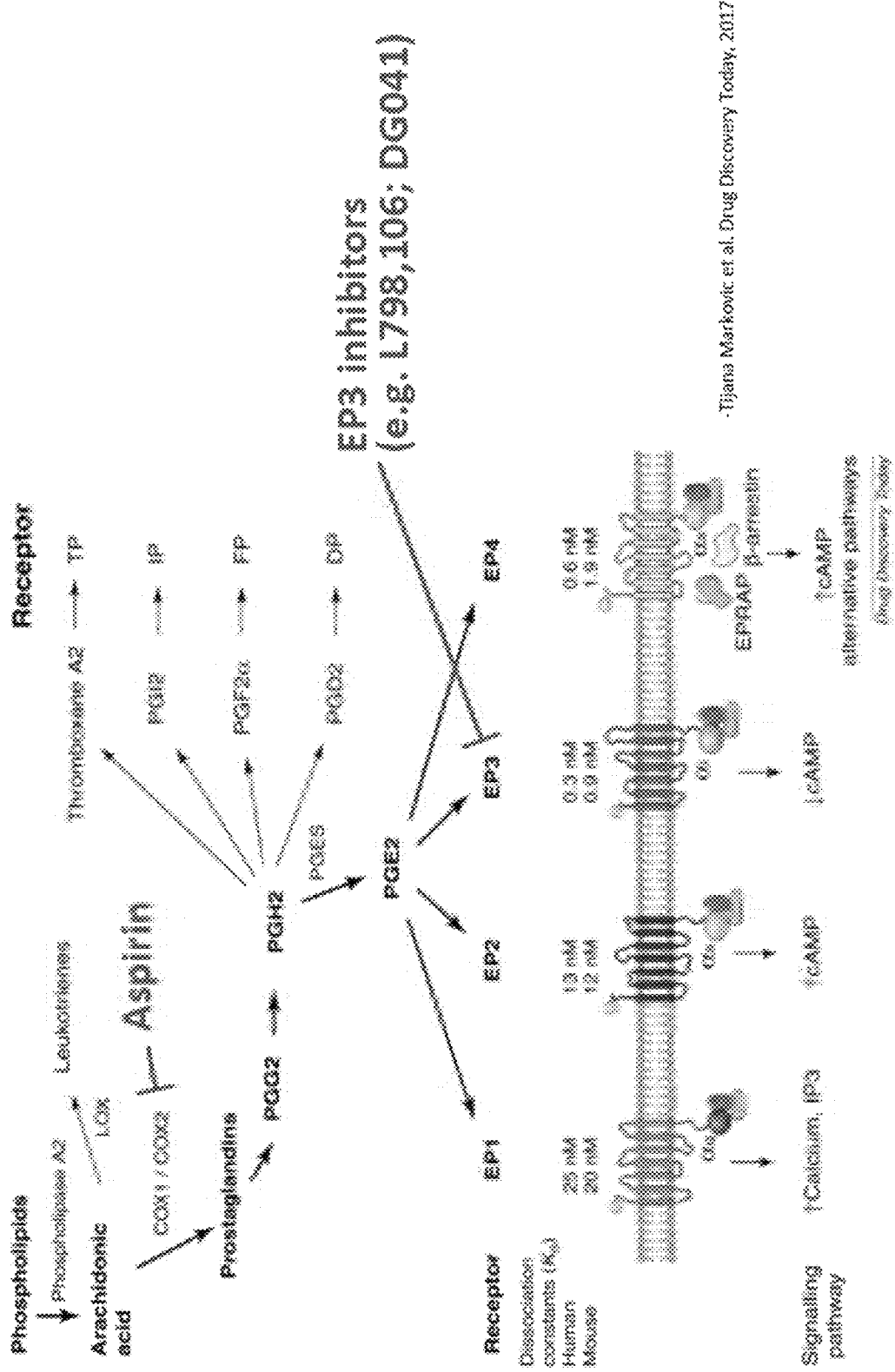
FIG. 12 shows an exemplary schematic of the PTGER3 (also known as EP3) signaling pathway.

FIG. 12 illustrates the PTGER3 pathway, including the portions of the signal pathway that are affected by aspirin and PTGER3 inhibitors L798,106 and DG041) based on an illustration from Markovic et al., Structural features of subtype-selective EP receptor modulators. Drug Discovery Today, Volume 22(1)-Jan. 1, 2017.

Figure 13:
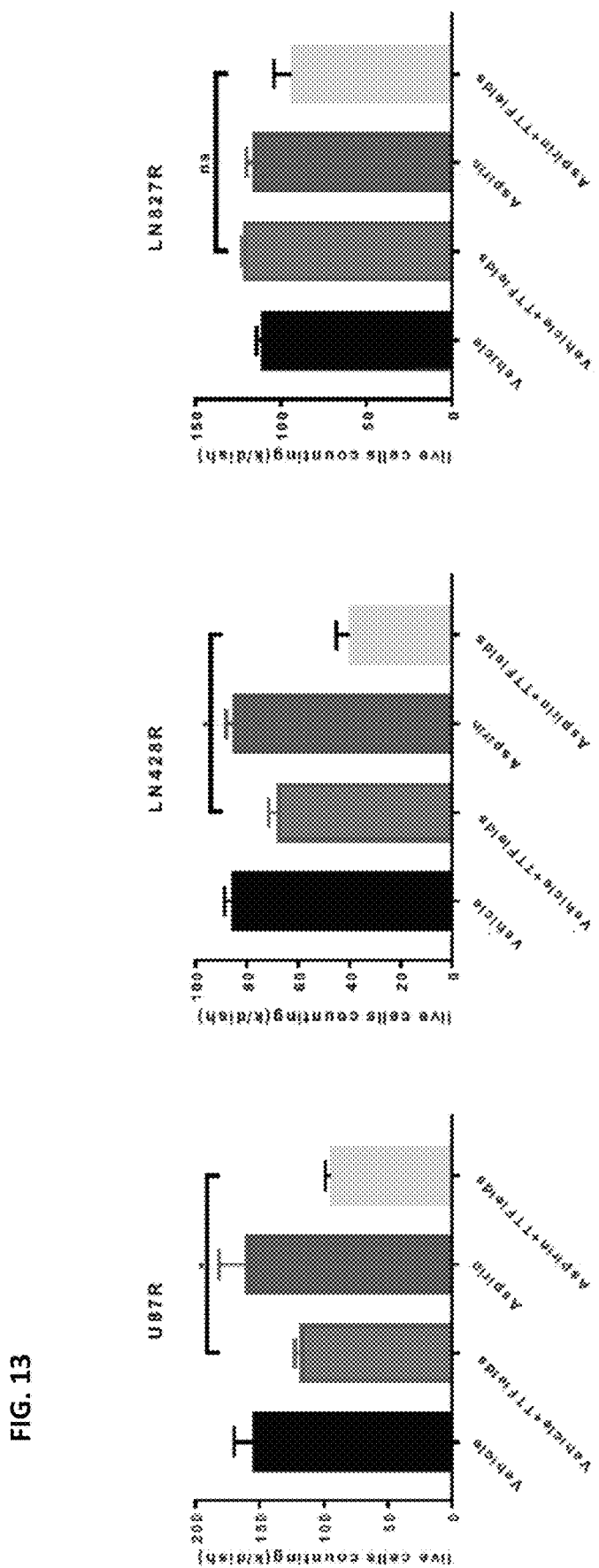
FIG. 13 shows that a PTGER3 inhibitor (aspirin) reduces resistance to TTFields in TTFields-resistant GBM cells.

Aspirin significantly reduces resistance to TTFields in TTFields-resistant cells. FIG. 13 shows that aspirin reduces resistance to TTFields in TTFields-resistant GBM cells (U87R, L428R, and LN827R) (compare Vehicle+TTFields to Aspirin+TTFields). For the experiments summarized in FIG. 13, resistant human GBM cells were treated with either vehicle control or aspirin and with or without TTFields for 3 days. Drug was replenished daily. The numbers of live cells were quantified using a cell counter at the end point.

Therefore, patients who develop resistance to TTFields treatments (e.g., over the course of long term use) can reduce resistance to TTFields by taking an aspirin (e.g., daily) enabling TTFields treatment to be more effective for a longer period of time. Without being bound by theory, it is believed that this approach can improve the effectiveness of TTFields in patients who develop resistance.

For example, in U87R resistant cells, TTFields reduced the live cell count from 150 k/dish to 125 k/dish. When aspirin was provided to the cells, the live cell count was reduced from 150 k/dish to 100 k/dish. In LN428R resistant cells, TTFields reduced the live cell count from 85 k/dish to 70 k/dish. When aspirin was provided to the cells, the live cell count was reduced from 85 k/dish to 40 k/dish. In LN827R cells, TTFields increased the live cell count slightly. When aspirin was provided to the cells, the live cell count was reduced from around 125 k/dish to 90 k/dish.

Figure 14:
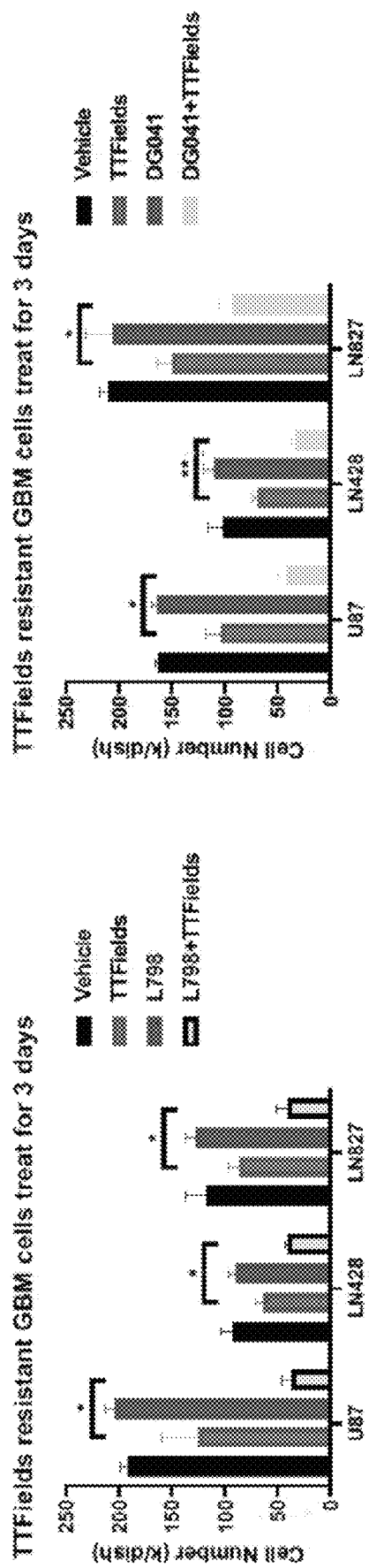
FIG. 14 shows that PTGER3 Inhibition restores the sensitivity of GBM resistant cells to TTFields.

PTGER3 inhibitors can restore sensitivity to TTFields. Resistant human GBM cells were treated with either the vehicle control or an EP3 (PTGER3) inhibitor (L798,106 (left panel) or DG041 (right panel) separately with or without TTFields at 200 kHz for 3 days (FIG. 14). DG041 was obtained from US Biological and L789,106 was obtained from Tocris. For the experiment summarized in FIG. 14, drugs were replenished daily. The number of live cells was quantified using a cell counter at the end point. As shown in FIG. 14, the PTGER3 inhibitors restores sensitivity to TTFields (compare TTFields bars to L798,106+TTFields and DG041+TTFields).

As shown in FIG. 14 (left panel), TTFields reduced the live cell count from around 200 k/dish to 125 k/dish for U87 GBM resistant cells. When PTGER3 inhibitor L798,106 (0.5 µM) was provided to the cells, the live cell count was reduced from around 200 k/dish to 25 k/dish. As shown in FIG. 14 (right panel), TTFields reduced the live cell count from around 160 k/dish to 100 k/dish for U87 GBM resistant cells. When PTGER3 inhibitor DG041 (50 nM) was provided to the cells, the live cell count was reduced from around 160 k/dish to around 40 k/dish. This data demonstrates that even after resistance to TTFields is developed, PTGER3 inhibitors can restore sensitivity to TTFields.

Figure 15A:
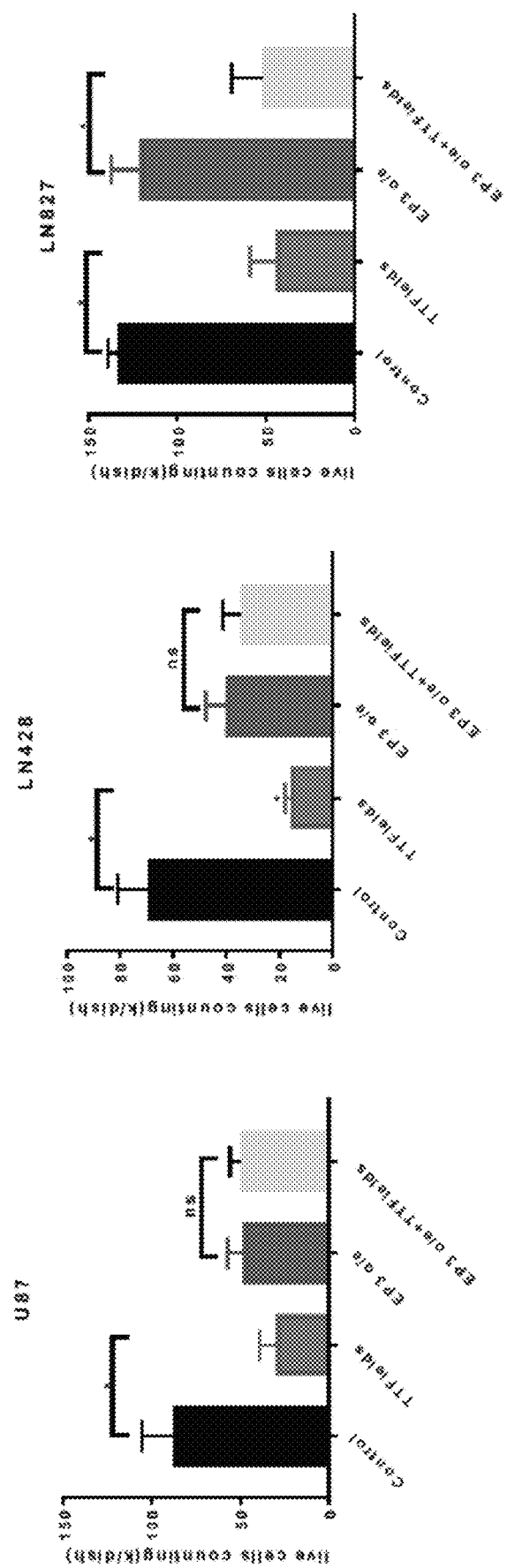
FIGS. 15A-15B show that forced PTGER3 expression in TTFields-sensitive GBM cells confers resistance to TTFields.
Figure 15B:
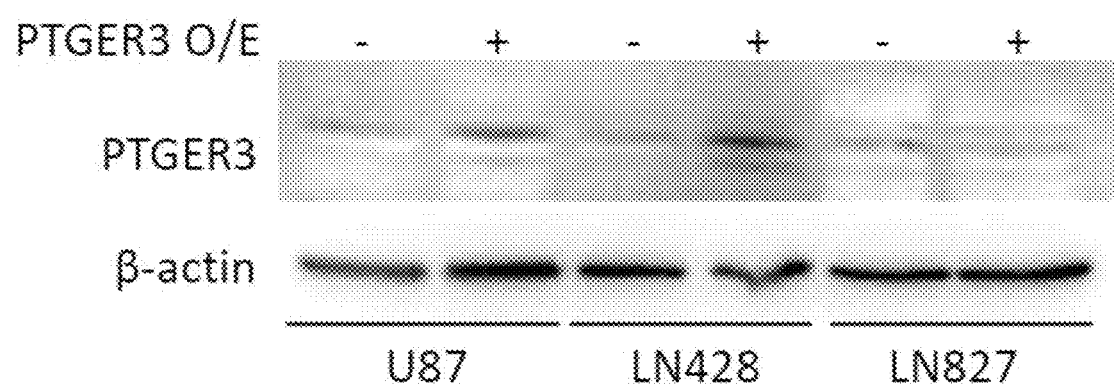

Forced PTGER3 expression in TTFields-sensitive GBM cells confers resistance to TTFields. As shown in FIG. 15A, human GBM cells were transduced with a lentivirus expressing an empty vector control (EV) or PTGER3 and subsequently treated with TTFields at 200 kHz for 3 days. The number of live cells was quantified using a cell counter. EP3 overexpression efficiency was determined by Western blot (FIG. 15B). Resistance was conferred only in cells that overexpressed EP3 (U87 and LN428) and not in cells that failed to overexpress EP3 (LN827).

Figure 16:
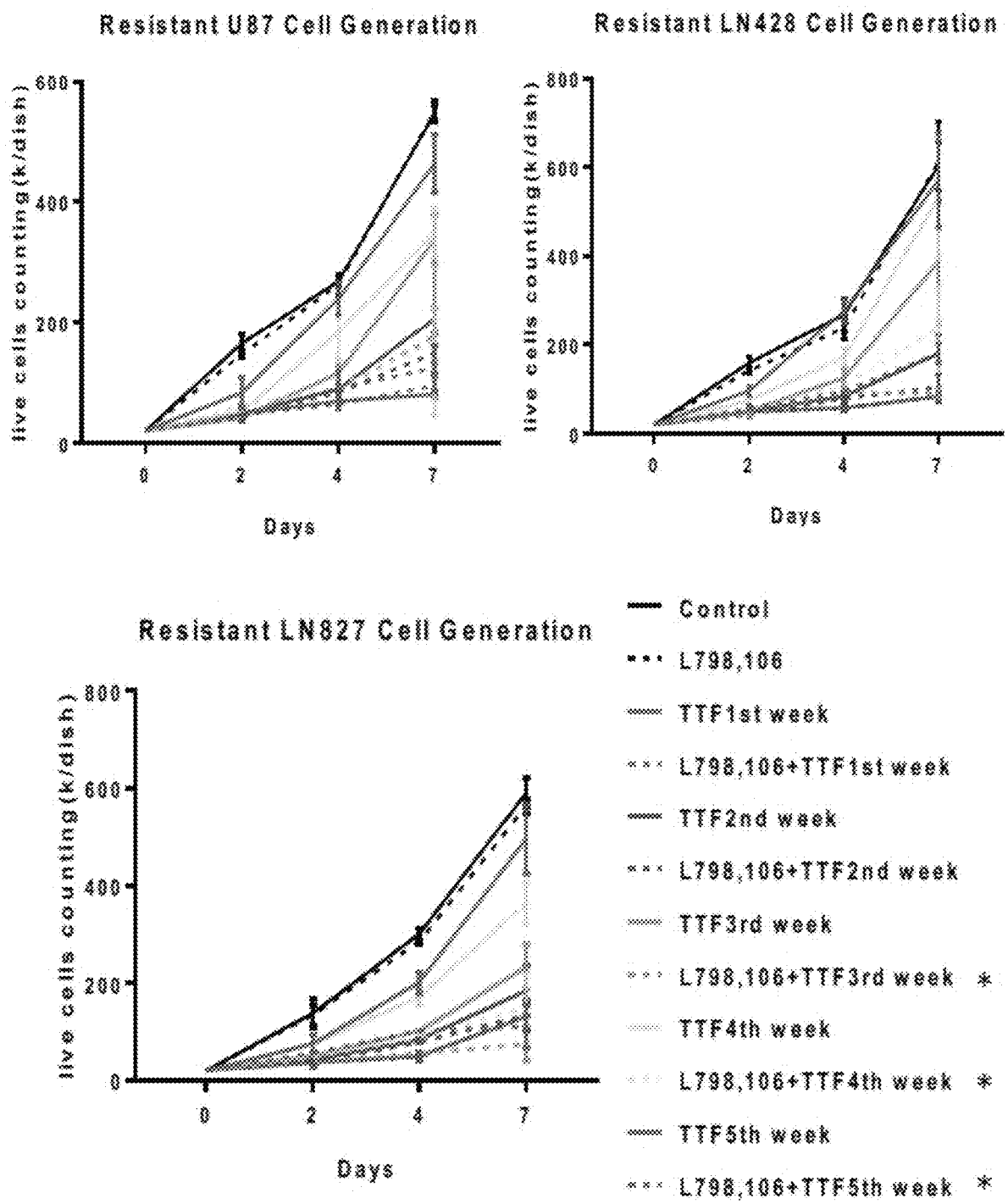
FIG. 16 shows that PTGER3 inhibition in TTFields-sensitive GBM Cells prevents the development of resistance to TTFields.

The resistant cell line generation experiment using the original human GBM cell lines from FIG. 2 was repeated with two more groups that included a PTGER3 inhibitor (L798,106 and L798,106+TTFields) (FIG. 16). The L798, 106 PTGER3 inhibitor prevented the development of resistance to TTFields. Cells were seeded and counted at the same cell density and time points. Each cycle lasts for 7 days within total of 5 cycles.

Figure 17:
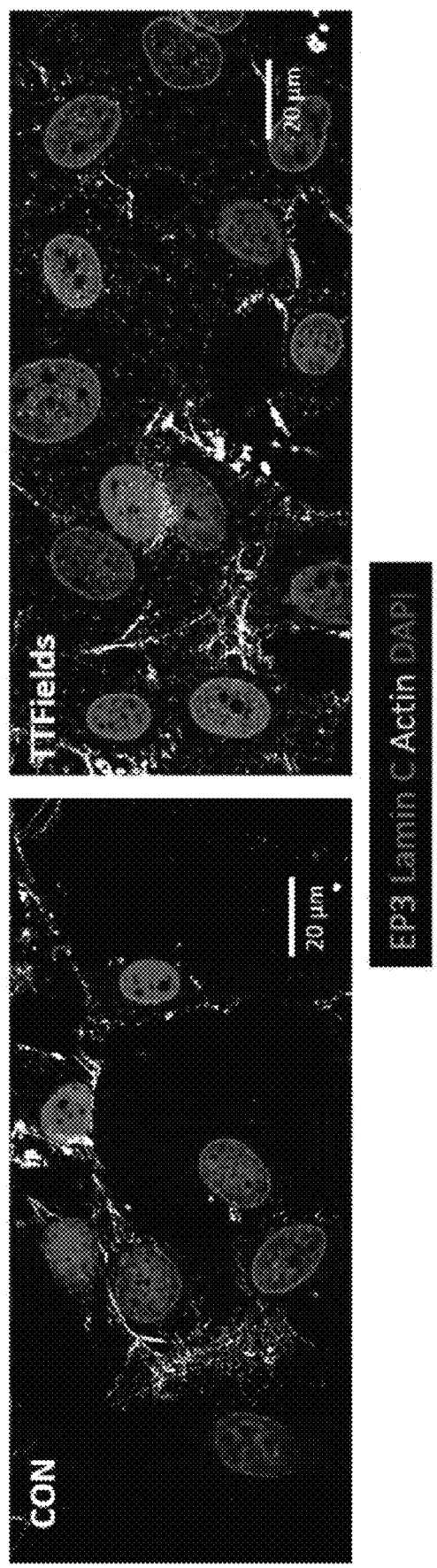
FIG. 17 shows that PTGER3 is upregulated and translocates to or is present in the nucleus (as shown by DAPI and limited by lamin A/C) in the initial exposure to TTFields.

The results shown in FIG. 17 demonstrate the presence of EP3 in the nucleus upon exposure to TTFields. These results show the presence or translocation of EP3, a 7 transmembrane cell surface receptor, to the nucleus where it acts as a master regulator of resistance to TTFields with direct interactions with hundreds of genes. The vast majority of master regulators are transcription factors localized to the nucleus.

Without being bound by theory, it is believed that EP3 is upregulated and either present or translocated to the nucleus upon exposure to TTFields providing a mechanism whereby EP3 can regulate other genes directly or indirectly through other transcription factors, such as the neuronal stem factor ZNF488. Therefore, it is believed that EP3 regulates resistance to TTFields by promoting the development and enrichment of GBM stem cells, which, due to their slow recycling rates and other survival and anti-apoptotic pathways, are resistant to many treatment modalities (e.g., TTFields).

Figure 18A:
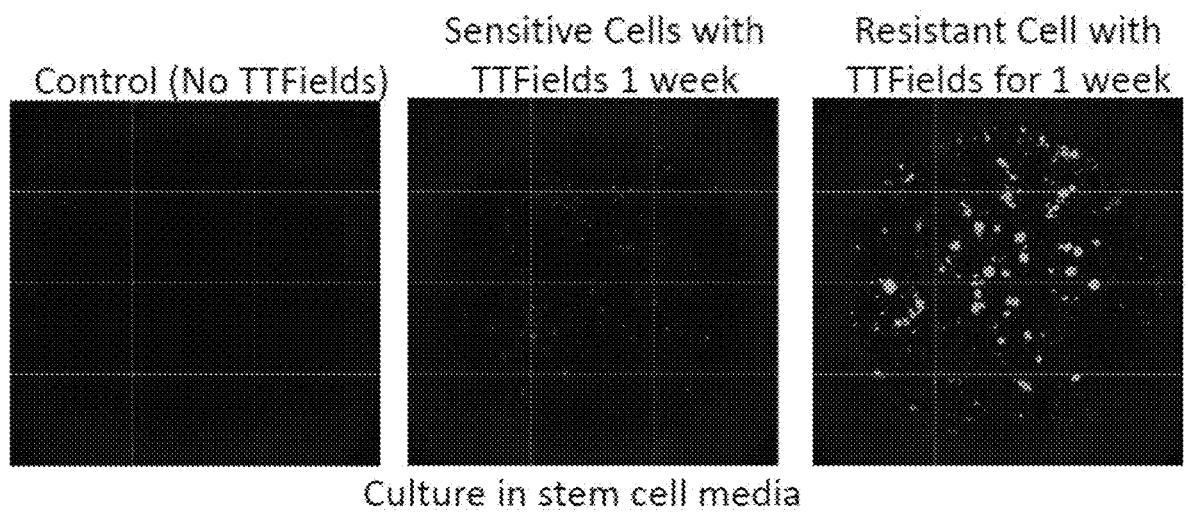
FIGS. 18A-18B shows that TTFields-resistant GBM cells are enriched in stemness phenotypes (demonstrated by increased gliomasphere formation and CD44 surface marker)
Figure 18B:
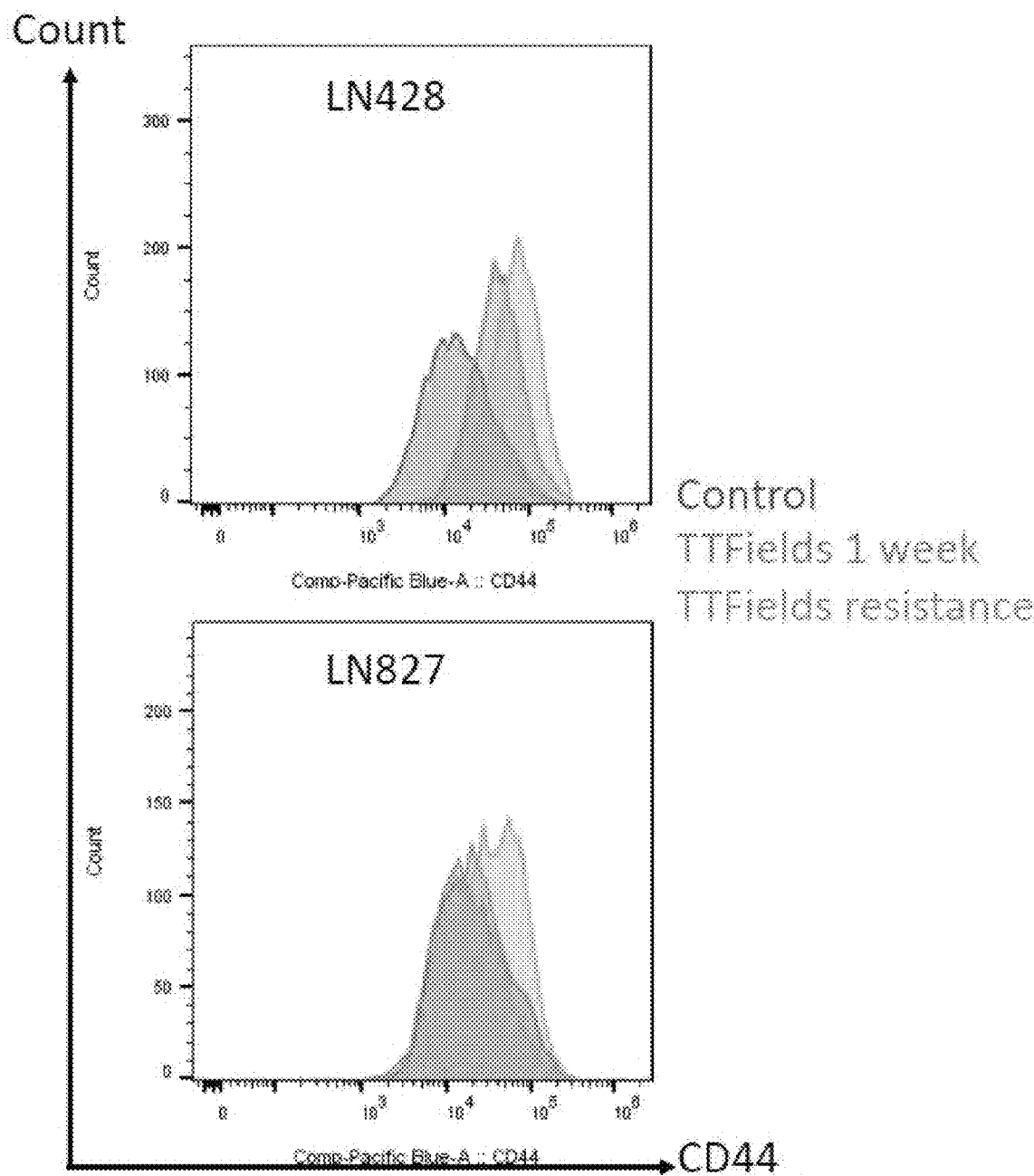

A shown in FIGS. 18A-18B, TTFields-resistant GBM cells are enriched in "sternness" phenotypes (e.g., gliomasphere formation and CD44 surface markers). FIG. 18A shows gliomasphere formation in resistant cells treated with TTFields for 1 week while TTFields-sensitive cells treated with TTFields for a week did not show gliomasphere formation.

FIG. 18B shows an increase in CD44 surface markers in TTFields resistant cells compared to TTFields-sensitive cells. Human GBM cell lines were treated as indicated, then seeded into 96-well plates at the density of 100 cells/well in FBS free stem cell culture media, cultured for 4 weeks and stained by Calcein AM dye for 30 min at room temperature. Images of each well were taken in pate reader (SpectraMax® i3x) at the wavelength of ex/em=456/541 nm. CD44 expression was measured by FACS.

Figure 19:
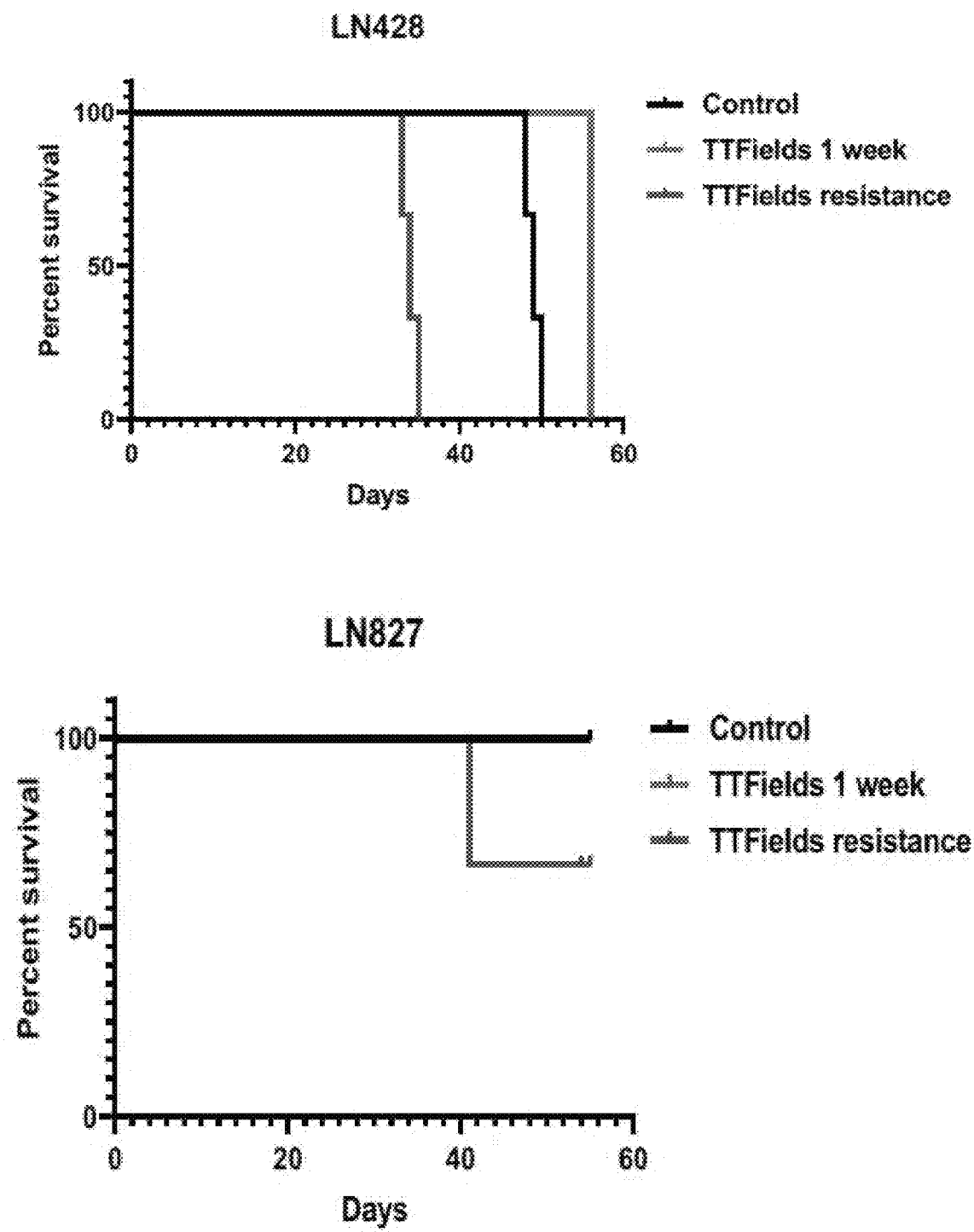
FIG. 19 show that TTFields-resistant cells are enriched in GBM stem cells, leading to increased tumor growth and death.

As shown in FIG. 19, TTFields-resistant cells are enriched in GBM stem cells leading to increased tumor growth and death. TTFields-resistant and TTFields-sensitive cells were implanted in the brains of mice. Equal number of cells in each treatment condition were implanted orthotopically in brain of NSG mice and survival was measured as a proxy for tumor growth.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of reducing viability of TTFields-resistant cancer cells in a subject, the method comprising:
    administering a Prostaglandin E Receptor 3 (PTGER3) inhibitor to the subject, wherein the PTGER3 inhibitor is selected from the group consisting of one or more of aspirin, ibuprofen, L798,106, and DG041; and
    applying an alternating electric field to the cancer cells of the subject, the alternating electric field having a frequency between 100 and 500 kHz,
    wherein the cancer cells are glioblastoma cells.

2. The method of claim 1, wherein the alternating electric field has a frequency between 100 and 300 kHz.

3. The method of claim 1, wherein the PTGER3 inhibitor is L798,106, or DG041.

4. The method of claim 1, wherein the PTGER3 inhibitor is aspirin or ibuprofen.

5. The method of claim 1, the PTGER3 inhibitor is administered to the subject at a concentration of from about 1 to 500 nanomolar for L798,106, or 0.1 to 2 millimolar for aspirin, or 0.5 to 50 nanomolar for DG041.

6. The method of claim 5, wherein the concentration of the PTGER3 inhibitor in the subject is maintained for at least about 3 days to 5 weeks.

* * * * *